United States Patent
Huth et al.

(10) Patent No.: US 7,122,547 B1
(45) Date of Patent: Oct. 17, 2006

(54) ANTHRANILIC ACID AMIDES AND THE USE THEREOF AS MEDICAMENTS

(75) Inventors: Andreas Huth, Berlin (DE); Dieter Seidelmann, Berlin (DE); Karl-Heinz Thierauch, Berlin (DE); Guido Bold, Gipf-Oberfrick (CH); Paul William Manley, Arlesheim (CH); Pascal Furet, Thann (FR); Jeanette Marjorie Wood, Biel-Benken (CH); Jürgen Mestan, Emmendingen (DE); Jose Brüggen, Reihen (CH); Stefano Ferrari, Muttenz (CH); Martin Krüger, Berlin (DE); Eckhard Ottow, Berlin (DE); Andreas Menrad, Oranienburg (DE); Michael Schirner, Berlin (DE)

(73) Assignees: Schering AG, Berlin (DE); Novartis AG, Basel (CH)

( * ) Notice: Subject to any disclaimer, the term of this patent is extended or adjusted under 35 U.S.C. 154(b) by 0 days.

(21) Appl. No.: 09/831,506

(22) PCT Filed: Nov. 9, 1999

(86) PCT No.: PCT/EP99/08478

§ 371 (c)(1),
(2), (4) Date: Sep. 14, 2001

(87) PCT Pub. No.: WO00/27819

PCT Pub. Date: May 18, 2000

(30) Foreign Application Priority Data

Nov. 10, 1998 (GB) .................................. 9824579
Mar. 3, 1999 (DE) ................................. 199 10 396

(51) Int. Cl.
*A61K 31/505* (2006.01)
*C07D 239/26* (2006.01)

(52) U.S. Cl. ................ 514/241; 514/256; 514/307; 514/311; 514/351; 514/357; 514/365; 514/374; 514/400; 514/406; 514/438; 514/469; 514/620; 544/215; 544/335; 546/146; 546/175; 546/300; 546/337; 548/205; 548/236; 548/238.1; 548/375.1; 549/77; 549/462; 549/493; 564/168

(58) Field of Classification Search ................ 546/337, 546/280.4, 277.4, 171, 265, 143, 268.7, 275.4, 546/282.4, 275.7, 270.1, 140; 514/357, 336, 514/339, 314, 332, 310, 272, 342, 341, 338, 514/308, 256, 307, 311, 351, 365, 374, 400, 514/406, 438, 469, 620; 544/331; 548/345.1, 548/238.1, 236, 205; 549/493, 462, 77; 564/168
See application file for complete search history.

(56) References Cited

U.S. PATENT DOCUMENTS 3,226,394 A * 12/1965 Schipper et al. ............ 260/295
3,409,668 A 11/1968 Palazzo ...................... 260/558
4,568,687 A 2/1986 Wright, Jr. et al.
5,716,993 A * 2/1998 Ozaki et al. ................ 514/619

FOREIGN PATENT DOCUMENTS

| DE | 2652144 A | 5/1978 |
|---|---|---|
| DE | 3406416 A1 | 8/1984 |
| EP | 0564356 A1 | 10/1993 |
| JP | 50157383 A | 12/1975 |

OTHER PUBLICATIONS

CAS printout for Wright et al. Chem. Abs. 102: 78876. (1985).*
CAS printout for Kovac et al. Chem Abs. 100: 34516 (1984).*
Carmellet and Jain, Angiogenesis in cancer and other diseases, Nature 407:249-257 (2000).*
Database Chemabs \377Online\377 Chemical Abstracts Service, Columbus, Ohio, US Montginoul, C. et al: "Analgesic anticonvulsant and anti-inflammatory activities of IH,3H-quinazoline-2,4-diones" retrieved from STN Database accession No. 110:165551h XP002135868 & Ann. Pharm. Fr. (1989), 46(4), 223-32.
Chemical Abstracts, vol. 85, No. 3, Jul. 19, 1976 (Jul. 19, 1976) Columbus, Ohio, US: abstract No. 21433p, Noda, Kanji et al: "Quinazoline compounds" Seite 701: XP002135867 & JP 50 157383 A (Hisamitsu Pharmaceutical Co., Ltd., Japan) Dec. 19, 1975 (Dec. 19, 1975).
Hardtmann, Goetz E. et al: "Chemistry of 2H-3, 1-benzoxazine-2,4(1H)-dione (isatoic anhydrides). 1. Synthesis of N-substituted 2H-3,1-benzoxazine-2,4(1H)-diones" Journal of Heterocyclic Chemistry., Bd. 12, Nr. 3, 1975, Seiten 565-572, XP002135866 Heterocorporation. Provo., US ISSN: 0022-152X.
Pastor, G. et al: "Synthesis of new 1H,3H-quinazoline-2,4-diones" Bulletin de la Societe Chimique de France., Bd. 5-6, Nr. 2, 1975, Seiten 1331-1338, XP002135865 Societe Francaise de Chimie. Paris., Fr ISSN: 0037-8968.
English Abstract of Hardtmann, Goetz E. et al: "Chemistry of 2H-3,1-benzoxazine-2,4(1H)-dione (isatoic anhydrides). 1. Synthesis of N-substituted 2H-3,1-benzoxazine-2,4(1H)-diones" Journal of Heterocyclic Chemistry., Bd. 12, Nr. 3, 1975, Seiten 565-572, XP002135866 Heterocorporation. Provo., US ISSN: 0022-152X.

(Continued)

*Primary Examiner*—James O. Wilson
*Assistant Examiner*—Paul V. Ward
(74) *Attorney, Agent, or Firm*—Millen, White, Zelano & Branigan, P.C.

(57) ABSTRACT

The invention relates to anthranilic acid amides and the use thereof as medicaments for the treatment of diseases that are triggered by persistent angiogenesis, in addition to intermediate products in the production of anthranilic acid amides.

14 Claims, No Drawings

OTHER PUBLICATIONS

English Abstract of Pastor, G. et al: "Synthesis of new 1H,3H-quinazoline-2,4-diones" Bulletin de la Societe Chimique de France., Bd. 5-6, Nr. 2, 1975, Seiten 1331-1338, XP002135865 Societe Francaise de Chimie. Paris., FR ISSN: 0037-8968.
English Abstract of JP 50157383 A.
English Abstract of DE 2652144 A.
English Abstract of EP 0564356 A1.
English Abstract of EP0564356A1: 4-phenylaminomethylimidazole derivatives, process for their preparation, angiotensin II receptor antagonists and their application in therapy [German][French], Dodey, Pierre et al. Jan. 4, 1992.

\* cited by examiner

ANTHRANILIC ACID AMIDES AND THE USE THEREOF AS MEDICAMENTS

This application is the national phase under 35 U.S.C. § 371 of PCT International Application No. PCT/EP99/08478 which has an International filing date of Nov. 9, 1999, which designated the United States of America.

The invention relates to anthranilic acid amides and their use as pharmaceutical agents for treatment of diseases that are triggered by persistent angiogenesis as well as their intermediate products for the production of anthranilic acid amides.

Persistent angiogenesis can be the cause of various diseases such as psoriasis, arthritis, such as rheumatoid arthritis, hemangioma, angiofibroma, eye diseases, such as diabetic retinopathy, neovascular glaucoma, renal diseases, such as glomerulonephritis diabetic nephropathy, malignant nephrosclerosis, thrombic microangiopathic syndrome, transplant rejections and glomerulopathy, fibrotic diseases, such as cirrhosis of the liver, mesangial-cell-proliferative diseases, and arteriosclerosis or can result in a progression of these diseases.

A direct or indirect inhibition of the VEGF receptor can be used for the treatment of such diseases and other VEGF-induced pathological angiogenesis and vascular permeable conditions, such as tumor vascularization. For example, it is known that by soluble receptors and antibodies against VEGF, the growth of tumors can be inhibited.

Persistent angiogenesis is induced by the VEGF factor via its receptor. So that VEFG can exert this action, it is necessary that VEGF bonds to the receptor and a tyrosine phosphorylation is brought about.

Phenyl-anthranilamide derivatives are already known that are used as angiotensin II-antagonists (EP 564 356) and as antiinflammatory agents and anti-ulcera compounds (U.S. Pat. No. 3,409,668).

It has now been found that compounds of general formula I

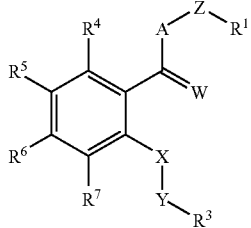

in which
A stands for the group $=NR^2$,
W stands for oxygen, sulfur, two hydrogen atoms or the group $=NR^8$,
Z stands for the group $=NR^{10}$ or $=N-$,
$-N(R^{10})-(CH_2)_q-$, branched or unbranched $C_{1-6}$ alkyl or the group

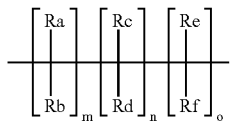

or A, Z and $R^1$ together form the group

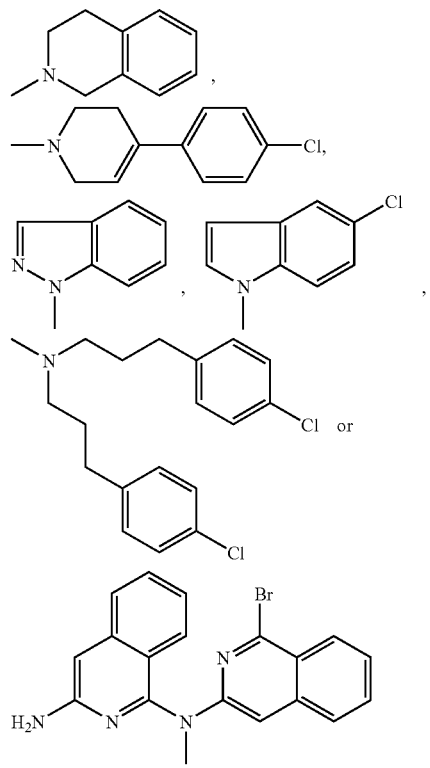

m, n and o stand for 0–3,
q stands for 1–6,
$R_a$, $R_b$, $R_c$, $R_d$, $R_e$, $R_f$ independently of one another, stand for hydrogen, $C_{1-4}$ alkyl or the group $=NR^{10}$, and/or $R_a$ and/or $R_b$ can form a bond with $R_c$ and/or $R_d$ or $R_c$ can form a bond with $R_e$ and/or $R_f$ or up to two of radicals $R_a$–$R_f$ can close a bridge with up to 3 C-atoms each to form $R^1$ or $R^2$,
X stands for the group $=NR^9$ or $=N-$,
Y stands for the group $-(CH_2)_p$,
p stands for 1–4,
$R^1$ stands for aryl or heteroaryl which is unsubstituted or, optionally substituted, one or more times with halogen, with $C_{1-6}$ alkyl, or with halogen substituted $C_{1-6}$ alkyl or $C_{1-6}$ alkoxy, with the exception of compounds in which aryl is bonded directly to the $=NR^2$ group in the meaning of A,
$R^2$ stands for hydrogen or $C_{1-6}$ alkyl or forms a bridge with up to 3 ring members with $R_a$–$R_f$ from Z or to form $R_1$,
$R^3$ stands for monocyclic or bicyclic aryl or heteroaryl that is unsubstituted or optionally substituted in one or more places with halogen, $C_{1-6}$ alkyl, $C_{1-6}$ alkoxy or hydroxy,
$R^4$, $R^5$, $R^6$, and $R^7$, independently of one another, stand for hydrogen, halogen, or $C_{1-6}$ alkoxy, $C_{1-6}$ alkyl or $C_{1-6}$ carboxylalkyl that is unsubstituted or optionally substituted in one or more places with halogen, or $R^5$ and $R^6$ together form the group

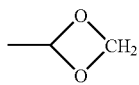

$R^8$, $R^9$, and $R^{10}$, independently of one another, stand for hydrogen or $C_{1-6}$ alkyl, as well as their isomers and salts, stop a tyrosine phosphorylation or persistent angiogenesis and thus prevent the growth and propagation of tumors.

If $R^2$ forms a bridge to $R^1$, heterocycles are produced to which $R^1$ is fused. For example, there can be mentioned:

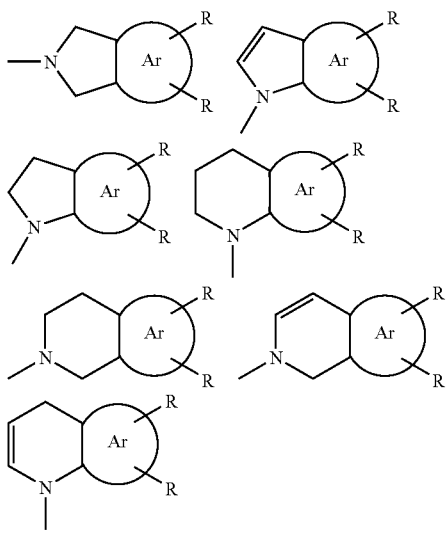

If $R_a$, $R_b$, $R_c$, $R_d$, $R_e$, $R_f$, independently of one another, represent hydrogen or $C_{1-4}$ alkyl, Z forms an alkyl chain.

If $R_a$ and/or $R_b$ form a bond with $R_c$ and/or $R_d$ or $R_c$ and/or $R_d$ form a bond with $R_e$ and/or $R_f$, Z stands for an alkenyl or alkinyl chain.

If $R_a$–$R_f$ form a bridge on their own, Z represents a cycloalkyl or cycloalkenyl group.

If up to two of radicals $R_a$–$R_f$ form a bridge with up to 3 C atoms to $R^1$, Z together with $R^1$ is a benzo- or hetaryl-condensed (Ar) cycloalkyl.

For example, there can be mentioned:

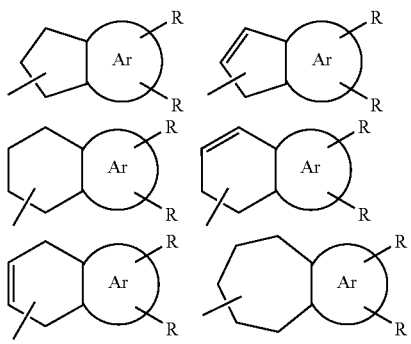

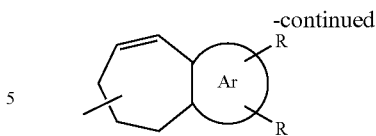

If one of radicals $R_a$–$R_f$ closes a bridge to form $R^2$, a nitrogen heterocycle that can be separated from $R^1$ by a group is formed.

For example, there can be mentioned:

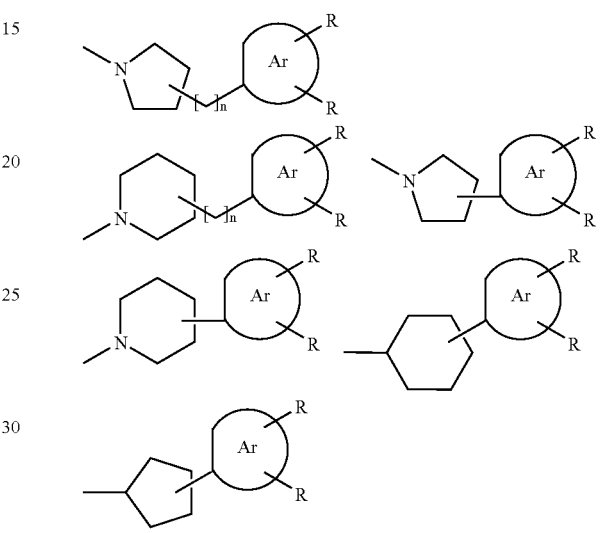

Alkyl is defined in each case as a straight-chain or branched alkyl radical, such as, for example, methyl, ethyl, propyl, isopropyl, butyl, isobutyl, sec-butyl, pentyl, isopentyl or hexyl, whereby $C_{1-4}$ alkyl radicals are preferred cycloalkyl is defined respectively as cyclopropyl, cyclobutyl, cyclopentyl, cyclohexyl or cycloheptyl.

Cycloalkenyl is defined respectively as cyclobutenyl, cyclopentenyl, cyclohexenyl, cycloheptenyl, whereby the linkage can take place both to the double bond and to the single bonds.

Halogen is defined respectively as fluorine, chlorine, bromine or iodine.

The alkenyl and alkinyl substituents are in each case straight-chain or branched and contain 2–6 C atoms, preferably 2–4 C atoms. For example, the following radicals can be mentioned: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, ethinyl, prop-1-in-1-yl, but-1-in-1-yl, but-2-in-1-yl, but-3-en-1-yl, allyl.

In each case, the aryl radical has 6–12 carbon atoms, such as, for example, naphthyl, biphenyl and especially phenyl.

In each case, the hetetoaryl radical can be benzocondensed. For example, there can be mentioned as 5-ring heteroaromatic compounds: thiophene, furan, oxazole, thiazole, imidazole, pyrazole and benzo derivatives thereof, and as 6-ring-heteroaromatic compounds pyridine, pyrimidine, triazine, quinoline, isoquinoline and benzo derivatives, whereby in the case of benzocondensed heteroaryl radicals, the binding can be both to the heterocycle and to the benzo ring.

In each case, the aryl radical and the heteroaryl radical can be substituted by the same or a different component in 1, 2 or 3 places with halogen, $C_{1-4}$ alkoxy, nitro, trifluoromethyl, trifluoromethoxy, cyano, $SO_qR^5$ or $C_{1-4}$ alkyl, whereby q stands for 0–2.

If an acid group is included, the physiologically compatible salts of organic and inorganic bases are suitable as salts, such as, for example, the readily soluble alkali and alkaline-earth salts as well as N-methyl-glucamine, dimethyl glucamine, ethyl glucamine, lysine, 1,6-hexadiamine, ethanolamine, glucosamine, sarcosine, serinol, tris-hydroxy-methyl-amino-methane, aminopropanediol, Sovak base, 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, i.a.

Those compounds of general formula I in which

A stands for the group $=NR^2$,

W stands for oxygen, sulfur, two hydrogen atoms or the group $=NR^8$,

Z stands for the group $=NR^{10}$, $=N-$ or $-N(R^{10})-(CH_2)_q-$, branched or unbranched $C_{1-6}$ alkyl or the group

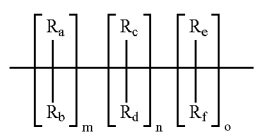

or A, Z and $R^1$ together form the group

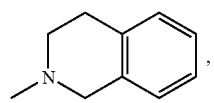

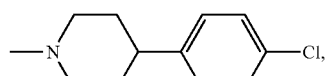 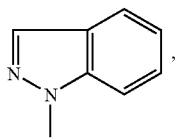

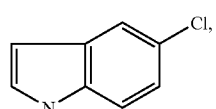

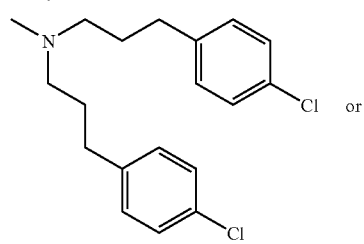

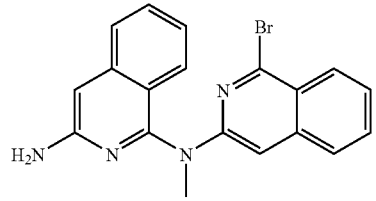

m, n, and o stand for 0–3, q stands for 1–6, $R_a$, $R_b$, $R_c$, $R_d$, $R_e$ and $R_f$ independently of one another, stand for hydrogen, $C_{1-4}$ alkyl or the group $=NR^{10}$, X stands for the group $=NR^9$ or $=N-$, Y stands for the group $-(CH_2)_p$, p stands for 1–4, $R^1$ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole, 6,7-dimethoxy-1,2,3,4-tetrahydro-2-naphthyl or for phenyl or pyridyl that is substituted in one or more places with $C_1$–$C_4$ alkyl, $C_1$–$C_4$ alkoxy, hydroxy, halogen, or trifluoromethyl, or for the group

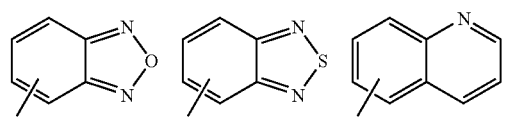

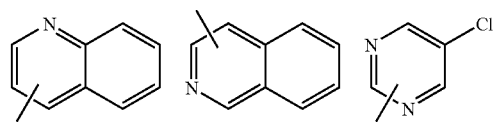

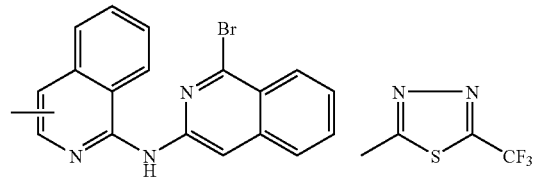

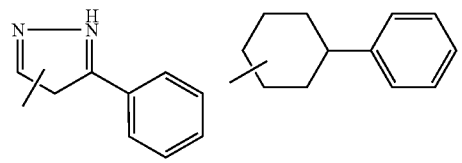

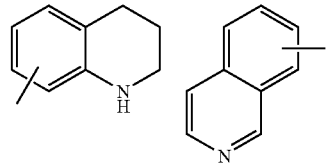

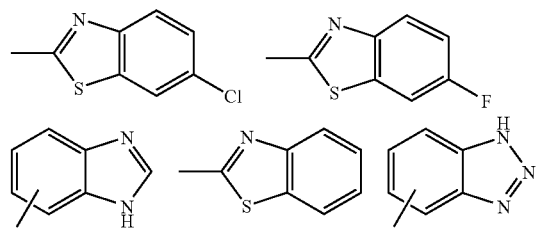

-continued

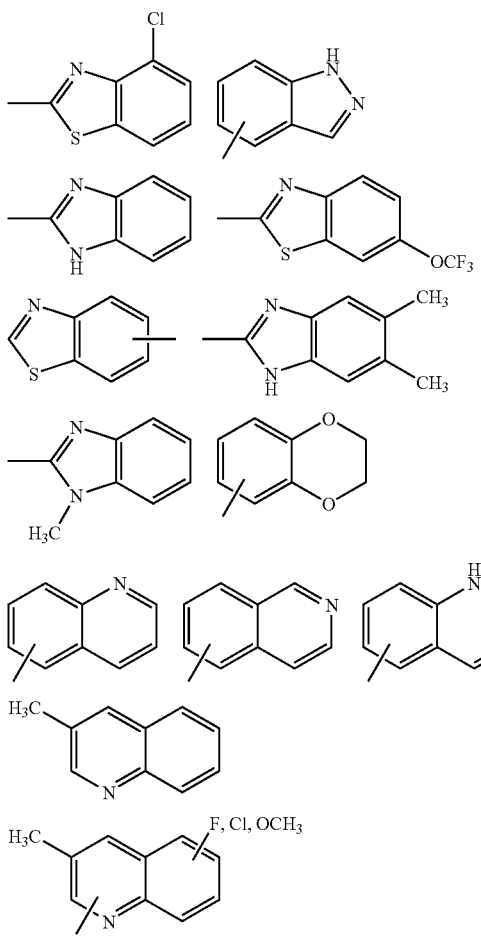

whereby phenyl, substituted phenyl or naphthyl is not right in the =NR² group in the meaning of A, R² stands for hydrogen or $C_{1-6}$ alkyl or forms a bridge with up to 3 ring members with $R_a$–$R_f$ from Z or to form R¹, R³ stands for monocyclic or bicyclic aryl or monocyclic or bicyclic heteroaryl that is unsubstituted or optionally substituted in one or more places with halogen, $C_{1-6}$ alkyl, $C_{1-6}$ alkoxy or hydroxy, R⁴, R⁵, R⁶ and R⁷, independently of one another, stand for hydrogen, halogen or $C_{1-6}$ alkoxy or $C_{1-6}$ alkyl that is unsubstituted or optionally substituted in one or more places with halogen, or R⁵ and R⁶ together form the group

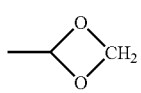

R⁸, R⁹ and R¹⁰, independently of one another, stand for hydrogen or $C_{1-6}$ alkyl, as well as their isomers and salts, have proven especially effective.

Also especially preferred are compounds of general formula I

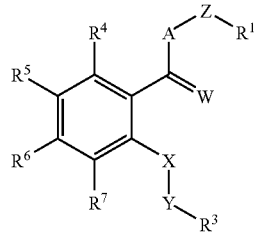

I in which
A stands for the group =NR²,
W stands for oxygen, sulfur or two hydrogen atoms,
Z stands for the group =NR¹⁰, =N—, —N(R¹⁰)—(CH₂)$_q$— or the group

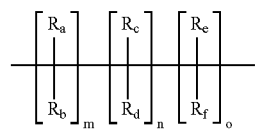

or A, Z and R¹ together form the group

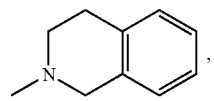

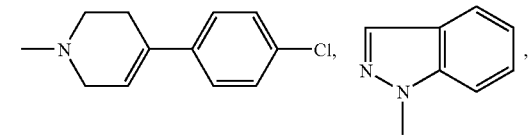

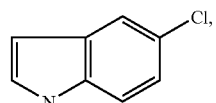

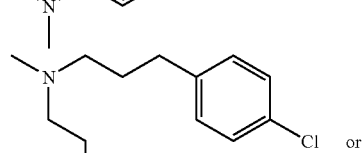

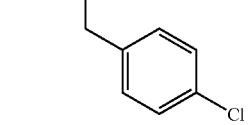

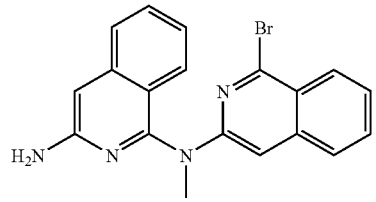

m, n and o stand for 0–3,
q stands for 1–6, $R_a$, $R_b$, $R_c$, $R_d$, $R_e$, $R_f$ independently of one another, stand for hydrogen or methyl or the group =NR$^{10}$, X stands for the group =NR$^9$ or =N—, Y stands for the group —CH$_2$—, $R^1$ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole, 6,7-dimethoxy-1,2,3,4-tetrahydro-2-naphthyl, or for phenyl or pyridyl that is substituted in one or more places with C$_1$–C$_4$ alkyl, C$_1$–C$_4$ alkoxy, hydroxy, halogen, trifluoromethyl, or for the group

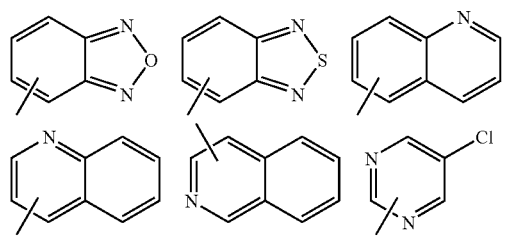

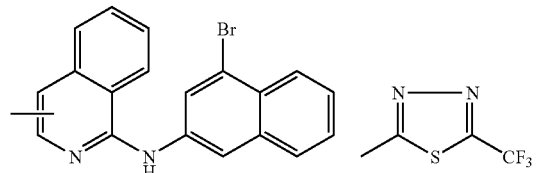

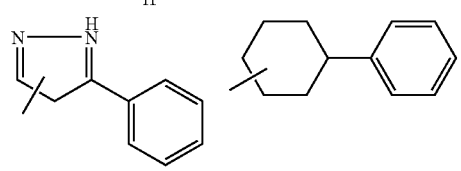

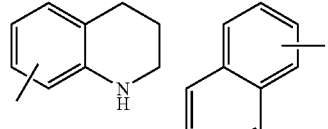

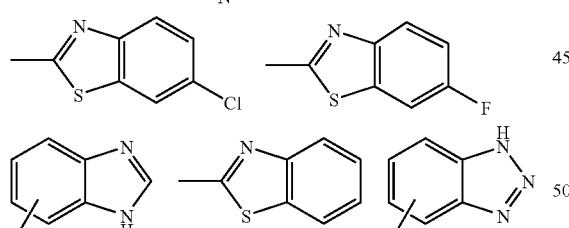

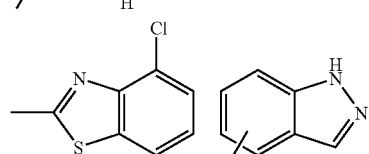

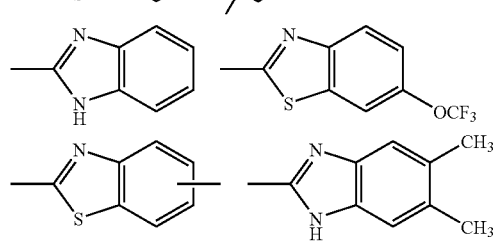

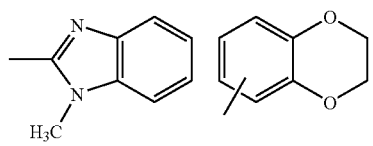

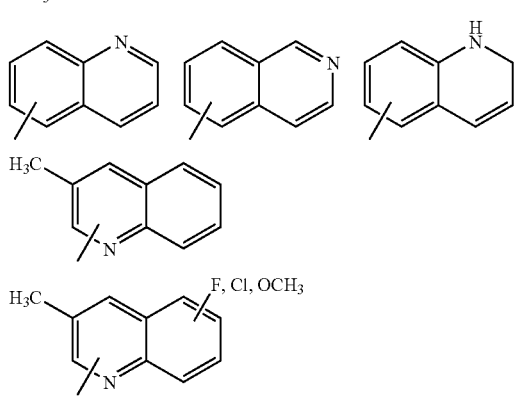

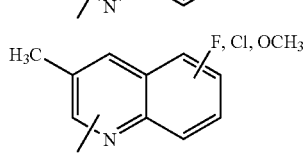

whereby phenyl, or substituted phenyl or naphthyl is not right in the =NR$^2$ group in the meaning of A, R$^2$ stands for hydrogen or methyl, R$^3$ stands for pyridyl or phenyl, pyridyl or 1,2,3,4-tetrahydronaphthyl that is substituted with hydroxy, halogen, methyl or methoxy, or the group

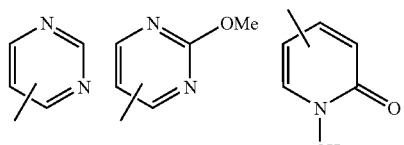

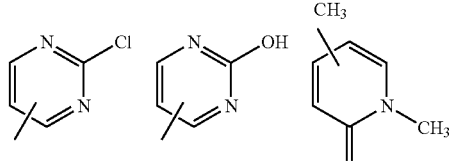

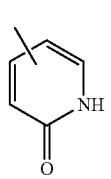

R$^5$ and R$^6$, independently of one another, stand for hydrogen, halogen, methyl, methoxy or trifluoromethyl, R$^4$ and R$^7$, independently of one another, stand for hydrogen or halogen, R$^9$ stands for hydrogen, R$^{10}$ stands for hydrogen or methyl, as well as their isomers and salts.

Those compounds of general formula I in which

A stands for the group =NR$^2$,

W stands for oxygen,

Z stands for the group =NR$^{10}$, =N—, —N(R$^{10}$)(CH$_2$) (CH$_2$)$_q$— or the group

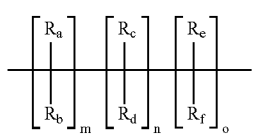

or A, Z and R¹ together form the group

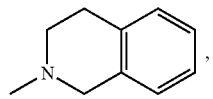

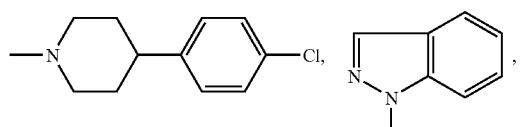

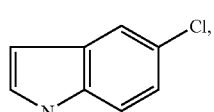

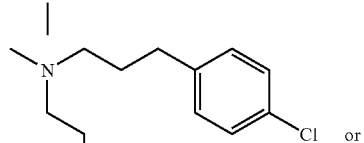

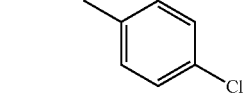

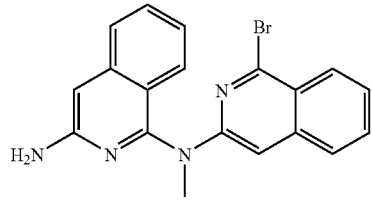

m, n and o stand for 0–3,
q stands for 1–6,
$R_a$, $R_b$, $R_c$, $R_d$, $R_e$, $R_f$ independently of one another, stand for hydrogen or methyl or the group $=NR^{10}$,
X stands for the group $=NR^9$ or $=N—$,
Y stands for the group $—CH_2—$,
R¹ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-naphthyl or for a phenyl or pyridyl that is substituted in one more places with $C_1$–$C_4$ alkyl, $C_1$–$C_4$ alkoxy, hydroxy, halogen, trifluoromethyl, or for the group

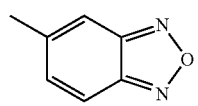 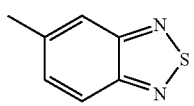

-continued

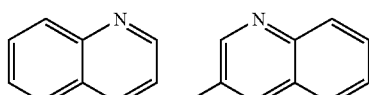

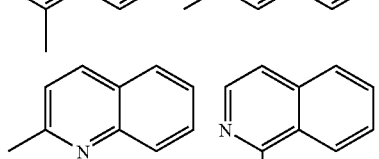

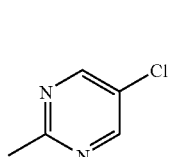

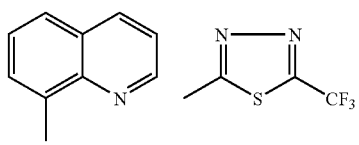

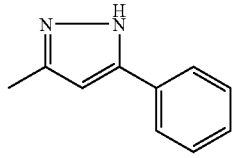

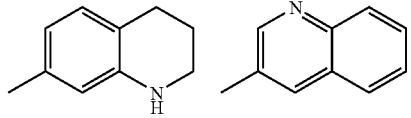

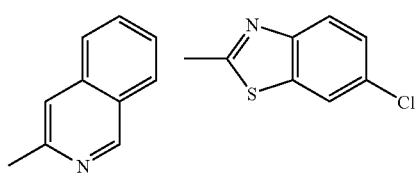

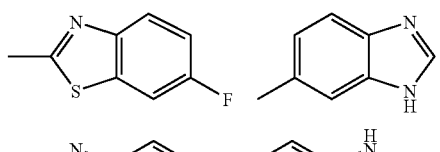

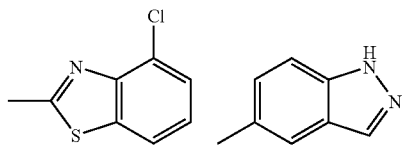

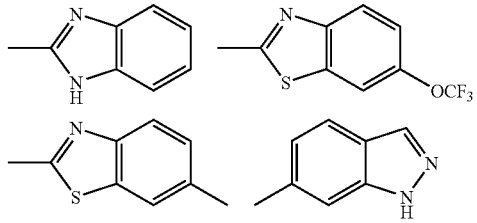

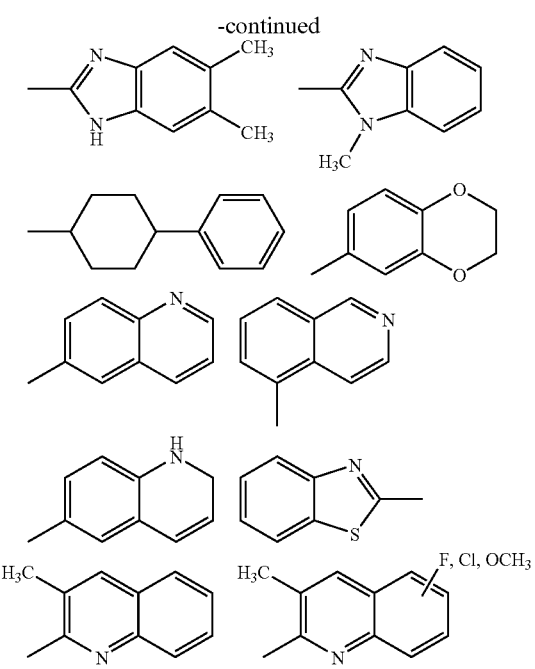

-continued

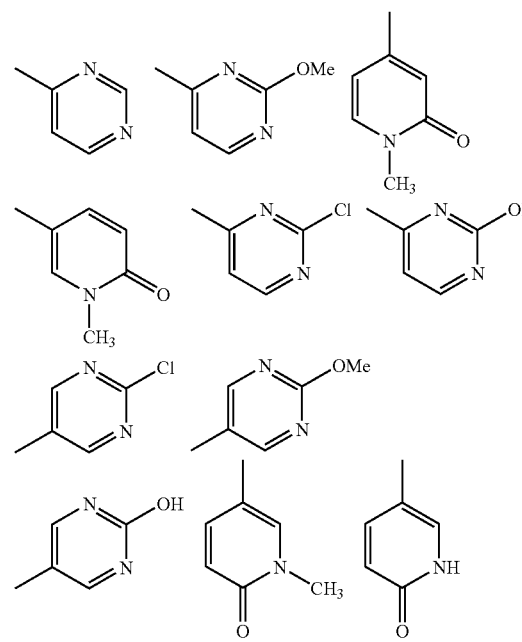

whereby phenyl, or substituted phenyl or naphthyl is not directly bonded to right in the =NR² group in the meaning of A, R² stands for hydrogen or methyl, R³ stands for pyridyl or for phenyl, pyridyl or 1,2,3,4-tetrahydronaphthyl that is substituted in one or more places with hydroxy, halogen, methyl or methoxy, or for the group

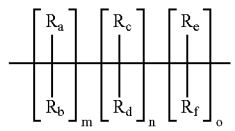

R⁵ and R⁶, independently of one another, stand for hydrogen, halogen, methyl, methoxy, or trifluoromethyl, R⁴ and R⁷, independently of one another, stand for hydrogen and halogen, R⁹ stands for hydrogen, R¹⁰ stands for hydrogen or methyl, as well as their isomers and salts, have proven quite especially effective.

Those compounds of general formula I in which

A stands for the group =NR²,

W stands for sulfur,

Z stands for the group =NR¹⁰, =N—, —N(R¹⁰)—(CH₂)_q— or the group $$\left[\begin{array}{c}R_a\\|\\R_b\end{array}\right]_m\left[\begin{array}{c}R_c\\|\\R_d\end{array}\right]_n\left[\begin{array}{c}R_e\\|\\R_f\end{array}\right]_o$$

or A, Z and R¹ together form the group

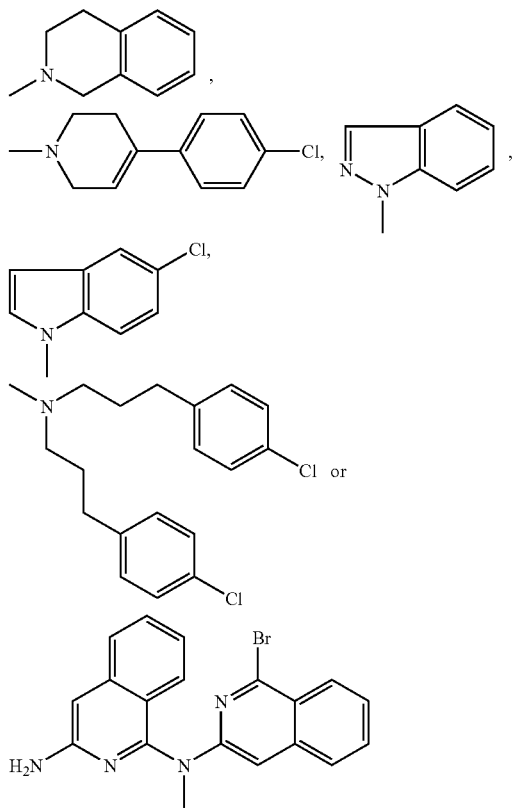

m, n and o stand for 0–3, q stands for 1–6, $R_a$, $R_b$, $R_c$, $R_d$, $R_e$, $R_f$, independently of one another, stand for hydrogen or methyl or the group =NR¹⁰, X stands for the group =NR⁹ or =N—, Y stands for the group —CH₂—, R¹ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-naphthyl or for phenyl or pyridyl that is substituted in one or more places with C₁–C₄ alkyl, C₁–C₄ alkoxy, hydroxy, halogen, trifluoromethyl, or for the group

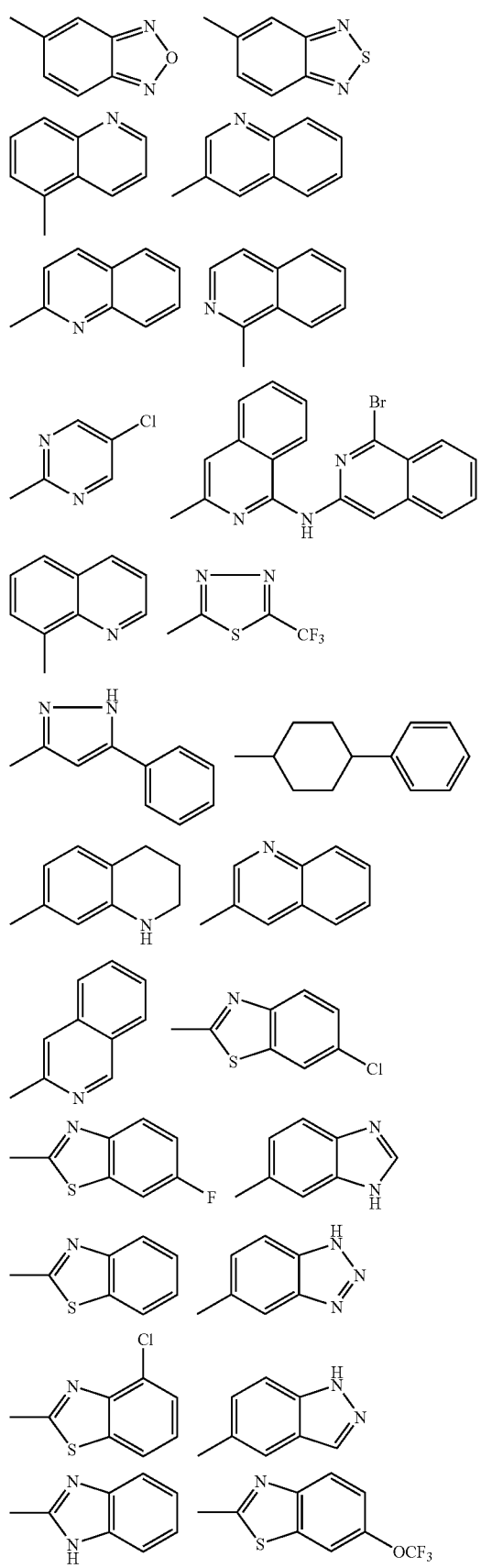
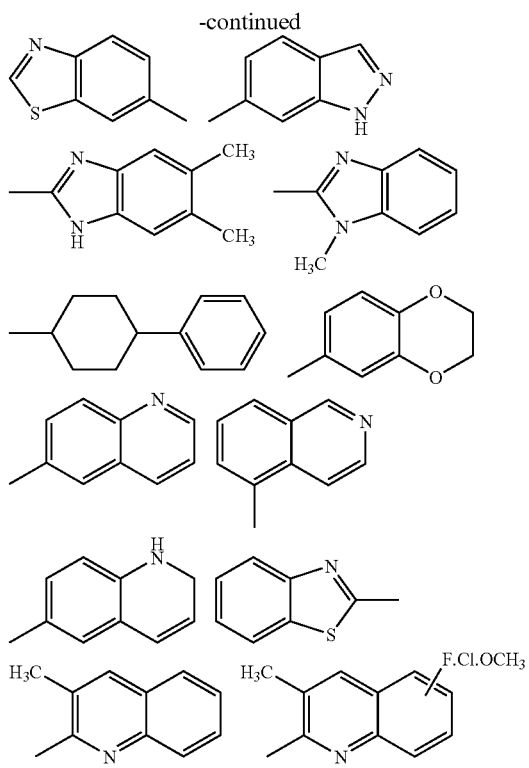
whereby phenyl, or substituted phenyl or naphthyl is not directly bonded to the =NR² group in the meaning of A,
R² stands for hydrogen or methyl,
R³ stands for pyridyl or for phenyl, pyridyl or 1,2,3,4-tetrahydronaphthyl that is substituted in one or more places with hydroxy, halogen, methyl or methoxy, or for the group
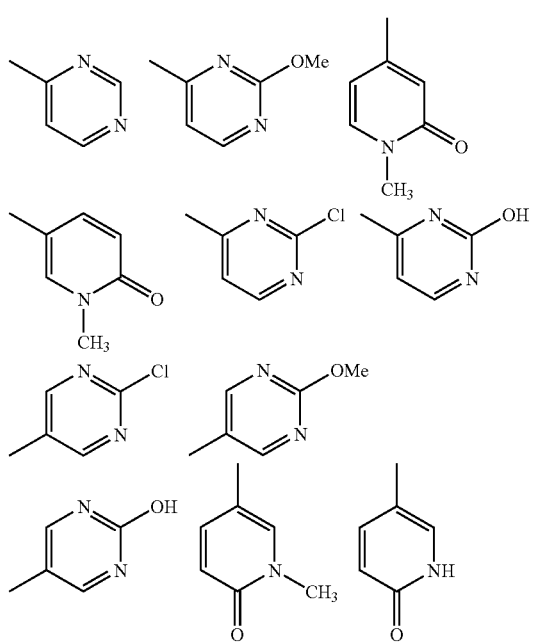

$R^5$ and $R^6$, independently of one another, stand for hydrogen, halogen, methyl, methoxy or trifluoromethyl,
$R^4$ and $R^7$, independently of one another, stand for hydrogen and halogen,
$R^9$ stands for hydrogen,
$R^{10}$ stands for hydrogen or methyl, as well as their isomers and salts, have also proven quite especially effective.

Those compounds of general formula I in which
A stands for the group $=NR^2$,
W stands for two hydrogen atoms,
Z stands for the group $=NR^{10}$, $=N-$, $-N(R^{10})(CH_2)_q-$ or the group

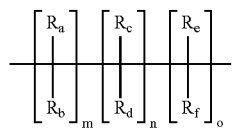

or A, Z, and $R^1$ together form the group

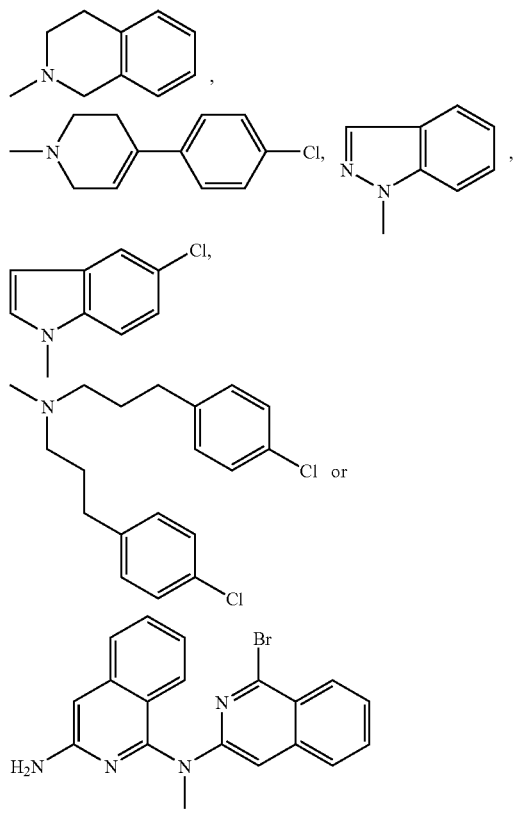

m, n and o stand for 0–3,
q stands for 1–6,
$R_a$, $R_b$, $R_c$, $R_d$, $R_e$, $R_f$ independently of one another, stand for hydrogen or methyl or the group $=NR^{10}$,
X stands for the group $=NR^9$ or $=N-$,
Y stands for the group $-CH_2-$,
$R^1$ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-naphthyl or for a phenyl or pyridyl that is substituted in one or more places with $C_1$–$C_4$ alkyl, $C_1$–$C_4$ alkoxy, hydroxy, halogen, or trifluoromethyl, or for the group

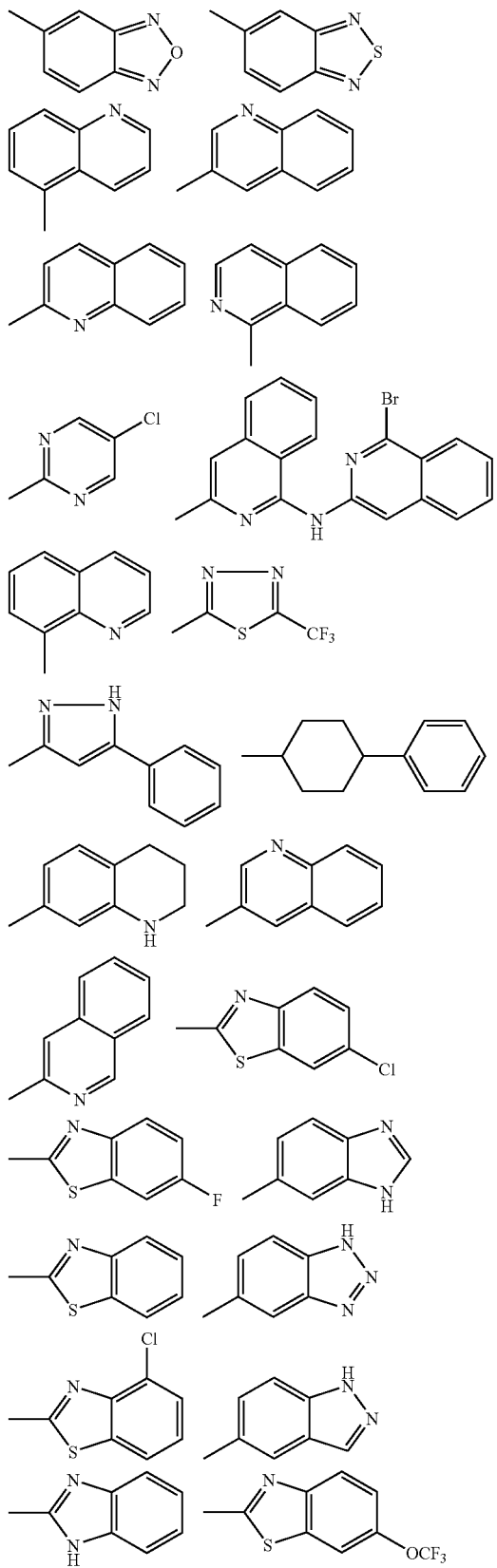

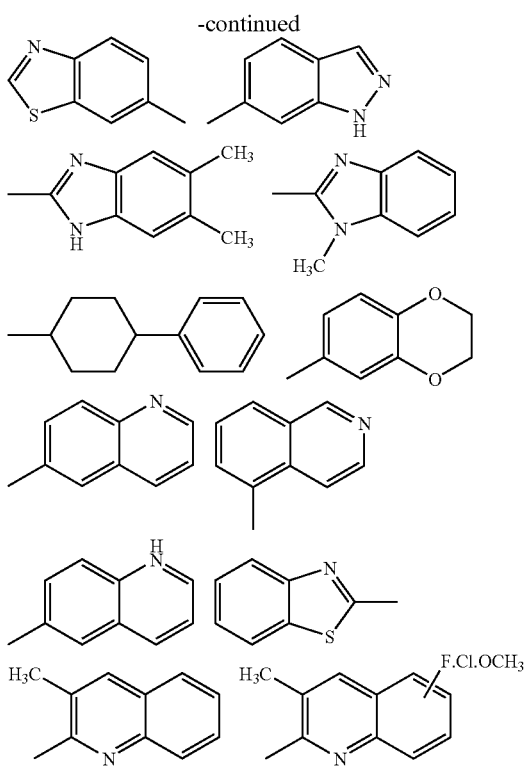

whereby phenyl, or substituted phenyl or naphthyl is not directly bonded to the =NR² group in the meaning of A, R² stands for hydrogen or methyl, R³ stands for pyridyl or for phenyl, pyridyl or 1,2,3,4-tetrahydronaphthyl that is substituted in one or more places with hydroxy, halogen, methyl or methoxy, or for the group

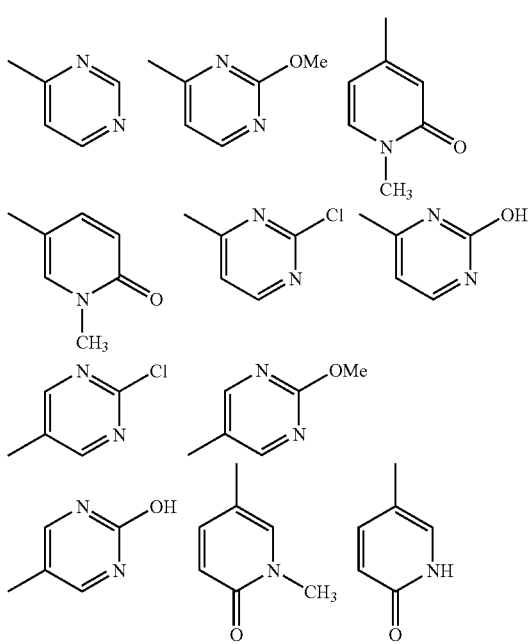

R⁴ and R⁷, independently of one another, stand for hydrogen, halogen, methyl, methoxy or trifluoromethyl, R⁵ and R⁶, independently of one another, stand for hydrogen and halogen, R⁹ stands for hydrogen, R¹⁰ stands for hydrogen or methyl, as well as their isomers and salts, have also proven quite especially effective.

The compounds according to the invention prevent a phosphorylation, i.e., certain tyrosine kinases can be inhibited selectively, whereby the persistent angiogenesis can be stopped. Thus, for example, the growth and the propagation of tumors is suppressed.

The compounds of general formula I according to the invention also include the possible tautomeric forms and comprise the E- or Z-isomers, or, if a chiral center is present, also the racemates and enantiomers.

The compounds of formula I and their physiologically compatible salts can be used based on their inhibitory activity relative to the phosphorylation of the VEGF receptor as a pharmaceutical agent. Based on their profile of action, the compounds according to the invention are suitable for the treatment of diseases that are caused by persistent angiogenesis.

Since the compounds of formula I are identified as inhibitors of the tyrosine kinases KDR and FLT, they are suitable in particular for treatment of those diseases that are caused by the persistent angiogenesis that is triggered by the VEGF receptor or an increase of vascular permeability.

The subject of this invention is also the use of compounds according to the invention as inhibitors of the tyrosine kinases KDR and FLT.

The subjects of this invention are thus also pharmaceutical agents for the treatment of tumors.

The compounds according to the invention can be used either alone or in a formulation as pharmaceutical agents for the treatment of psoriasis, arthritis, such as rheumatoid arthritis, hemangioma, angiofibroma, eye diseases, such as diabetic retinopathy, neovascular glaucoma, renal diseases, such as glomerulonephritis, diabetic nephropathy, malignant nephrosclerosis, thrombic microangiopathic syndrome, transplant rejections and glomerulopathy, fibrotic diseases, such as cirrhosis of the liver, mesangial-cell-proliferative diseases, arteriosclerosis and injuries to the nerve tissue.

The compounds according to the invention can also be used in inhibiting the reocclusion of vessels after balloon catheter treatment, in vascular prosthetics or after mechanical devices are used to keep vessels open, such as, e.g., stents.

In the treatment of injuries to the nerve tissue, a quick scar formation at the injury sites can be prevented with the compounds according to the invention, i.e., scars are prevented from forming before the axons are reconnected to one another. Reconstruction of the nerve connections thus would be facilitated.

The ascites formation in patients also can be suppressed with the compounds according to the invention. The VEGF-induced edemas can also be suppressed.

Such pharmaceutical agents, their formulations and uses are also the subject of this invention.

The invention also relates to the use of the compounds of general formula I, for the production of a pharmaceutical agent for treatment of tumors, psoriasis, arthritis, such as rheumatoid arthritis, hemangioma, angiofibroma, eye diseases, such as diabetic retinopathy, neovascular glaucoma, renal diseases, such as glomerulonephritis, diabetic nephropathy, malignant nephrosclerosis, thrombic microangiopathic syndrome, transplant rejections and glomerulopathy, fibrotic diseases, such as cirrhosis of the liver, mesangial-cell-proliferative diseases, arteriosclerosis, injuries to the nerve tissue, inhibition of the reocclusion of vessels after balloon catheter treatment, in vascular prosthetics or after mechanical devices are used to keep vessels open, such as, e.g., stents.

To use the compounds of formula I as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, capsules or in liquid form, for example as solutions, suspensions or emulsions. Moreover, they optionally contain adjuvants such as preservatives, stabilizers, wetting agents or emulsifiers, salts for changing osmotic pressure or buffers.

For parenteral use, in particular injection solutions or suspensions, especially aqueous solutions of the active compounds in polyhydroxyethoxylated castor oil, are suitable.

As vehicle systems, surface-active adjuvants, such as salts of bile acids or animal or plant phospholipids, but also mixtures thereof as well as liposomes or components thereof can also be used.

For oral use, especially tablets, coated tablets or capsules with talc and/or hydrocarbon vehicles or binders, such as, for example, lactose, corn or potato starch, are suitable. The application can also be carried out in liquid form, such as, for example, as juice, to which optionally a sweetener is added.

The dosage of the active ingredients can vary depending on the method of administration, age and weight of the patient, type and severity of the disease that is to be treated, and similar factors. The daily dose is 0.5–1000 mg, preferably 50–200 mg, whereby the dose can be given as a single dose to be administered once or subdivided into 2 or more daily doses.

The above-described formulations and forms for dispensing are also the subject of this invention.

The production of the compounds according to the invention is carried out according to methods that are known in the art. For example, compounds of formula I are obtained in that a) A compound of formula II

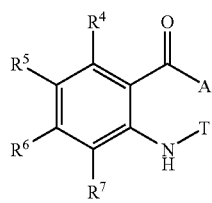

II

-continued

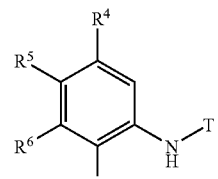

III

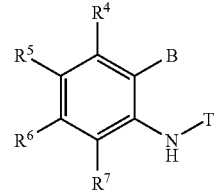

IV in which $R^4$ to $R^7$ have the above meaning and T is H or a protective group and A is halogen or $OR^{13}$, whereby $R^{13}$ means a hydrogen atom, $C_{1-4}$ alkyl or $C_{1-4}$ acyl, or a ring connects with T, first alkylates N and then converts COA into an amide and then optionally protective groups are cleaved or first converted into the amide and then N-alkylated, or b) A compound of formula III in which $R^4$ to $R^7$ have the above meaning and T means H or a protective group, is in orthometallated form, and then is converted into an amide by being caught with an electrophile, then the protective group is cleaved, and the amino group is alkylated, or c) A compound of formula IV in which $R^4$ to $R^7$ have the above meaning, and T means H or a protective group and B means halogen or O-filtrate, O-tosylate or O-mesylate, is converted into an amide, then the protective group is cleaved off, and the amino group is alkylated.

The sequence of the steps can be reversed in all three cases.

The amide formation is carried out according to methods that are known in the literature.

For amide formation, a start can be made from a corresponding ester. The ester is reacted according to J. Org. Chem. 1995, 8414 with aluminum trimethyl and the corresponding amine in solvents, such as toluene, at temperatures of 0° C. up to the boiling point of the solvent. This method can also be used in unprotected anthranilic acid esters. If the molecule contains two ester groups, both are converted into the same amide.

When nitrites are used instead of ester, amidines are obtained under analogous conditions.

For amide formation, however, all processes that are known from peptide chemistry are also available. For example, the corresponding acid can be reacted in aprotic polar solvents, such as, for example, dimethylformamide on an activated acid derivative, that can be obtained, for example, with hydroxybenzotriazole and a carbodiimide such as, for example, diisopropylcarbodiimide or else with preformed reagents, such as, for example, HATU (Chem. Comm. 1994, 201) or BTU, at temperatures of between 0° C. and the boiling point of the solvent, preferably at 80° C. with the amine at HATU preferably at room temperature. These methods can also be used in the unprotected anthranilic acids. For amide formation, the process can also be used on the mixed acid anhydride, imidazolide or azide. A prior protection of the amino group, for example as amide, is not necessary in all cases, but can affect the reaction advantageously. Isatoic acid anhydrides, in which the protection of the amino group and the activation of the acidic function are present at the same time, are a special starting material.

If the amine is already converted into the BOC-protected compound, the ortho-position can be metallated by reaction with organometallic compounds, such as, for example, n-butyllithium, and then caught with isocyanates or isothiocyanates to form the anthranilamides or anthranilthioamides. A bromine or iodine substituent in this ortho-position facilitates the ortho-metallation by halogen-metal exchange. As solvents, ethers such as diethyl ether or tetrahydrofuran or hydrocarbon such as hexane, but also mixtures thereof, are suitable. The addition of complexing agents, such as tetramethylethylenediamine (TMEDA) is advantageous. The temperatures vary between −78° C. and room temperature. The cleavage of the BOC-amides is carried out by treatment with acids, such as trifluoroacetic acid without solvent, or in solvents, such as methylene chloride, at temperatures of 0° C. up to the boiling point of the solvent or with aqueous hydrochloric acid, preferably 1N hydrochloric acid, in solvents such as ethanol or dioxane at temperatures from room temperature up to the boiling point of the solvent.

The amide group can also be introduced by carbonylation, however. To this end, a start is made from the corresponding compounds of formula IV (o-iodine, o-bromine or o-triflyloxyanilines), which are reacted with carbon monoxide at normal pressure or else increased pressure and an amine in the presence of transition metal catalysts, such as, for example, palladium(II) chloride or palladium(II) acetate or else palladium tetrakis triphenylphosphine in solvents such as dimethylformamide. The addition of a ligand such as triphenylphosphine and the addition of a base such as tributylamine can be advantageous-(see, for example, J. Org. Chem. 1974, 3327; J. Org. Chem. 1996, 7482; Synth. Comm. 1997, 367; Tetr. Lett 1998, 2835).

If various amide groups are to be introduced into the molecule, the second ester group must be introduced into the molecule, for example, after the production of the first amide group, and then must be amidated, or there is a molecule in which one group is present as ester and the other as acid, and the two groups are amidated in succession according to various methods.

Thioamides can be obtained from the anthranilamides by reaction with diphosphadithianes according to Bull Soc. Chim. Belg. 87, 229, 1978 or by reaction with phosphorus pentasulfide in solvents such as pyridine or else without solvent at temperatures of 0° C. to 200° C.

As electron rich aromatic compounds, the products can also be subjected to electrophilic aromatic substitutions. The substitution is then carried out in the ortho- or para-position to form the amino group or one of the amino groups. It can thus be acylated by Friedel-Crafts acylation with acid chlorides in the presence of Friedel-Crafts catalysts, such as, for example, aluminum trichloride in solvents such as nitromethane, carbon disulfide, methylene chloride or nitrobenzene at temperatures of between 0° C. and the boiling point of the solvent, preferably at room temperature.

One or more nitro groups can be introduced according to processes that are known in the literature, for example, by nitrating acid, various concentrated nitric acids without solvent or by metal nitrates, such as, for example, copper(II) nitrate or iron(III) nitrate in polar solvents, such as ethanol or glacial acetic acid or else in acetic anhydride.

The introduction of the halogens is carried out according to processes that are known in the literature, e.g., by reaction with bromine, N-bromine, or N-iodosuccinimide or urotropin hydrotribromide in polar solvents, such as tetrahydrofuran, acetonitrile, methylene chloride, glacial acetic acid or dimethylformamide.

The reduction of the nitro group is performed in polar solvents at room temperature or elevated temperature. As catalysts for the reduction, metals such as Raney nickel or noble metal catalysts such as palladium or platinum or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used, such as complex metal hydrides, optionally in the presence of heavy metal salts. Iron can also be used as a reducing agent. The reaction is then performed in the presence of an acid, such as, e.g., acetic acid or ammonium chloride, optionally with the addition of a solvent, such as, for example, water, methanol, etc. In the case of extended reaction time, acylation of the amino group can occur in this variant.

If an alkylation of an amino group is desired, alkylation can be done according to commonly used methods—for example with alkyl halides—or according to the Mitsunobu variant by reaction with an alcohol in the presence of, for example, triphenylphosphine and azodicarboxylic acid ester. The amine can also be subjected to reductive alkylation with aldehydes or ketones, whereby it is reacted in the presence of a reducing agent, such as, for example, sodium cyanoborohydride in a suitable inert solvent, such as, for example, ethanol, at temperatures of 0° C. up to the boiling point of the solvent. If a start is made from a primary amino group, a reaction can be carried out optionally in succession with two different carbonyl compounds, whereby mixed derivatives are obtained [literature, e.g., Verardo et al. Synthesis (1993), 121; Synthesis (1991), 447; Kawaguchi, Synthesis (1985), 701; Micovic et al. Synthesis (1991), 1043].

It may be advantageous to form the Schiff base first by reaction of the aldehyde with the amine in solvents such as ethanol or methanol, optionally with the addition of adjuvants such as glacial acetic acid, and then to add only reducing agent, such as, e.g., sodium cyanoborohydride.

The hydrogenation of alkene or alkine groups in the molecule is carried out in the usual way by, for example, catalytically activated hydrogen. As catalysts, heavy metals such as palladium or platinum, optionally on a vehicle or Raney nickel, can be used. As solvents, alcohols, such as, e.g., ethanol, are suitable. The procedure is performed at temperatures of 0° C. up to the boiling point of the solvent and at pressures of up to 20 bar, but preferably at room temperature and normal pressure. By using catalysts, such as, for example, a Lindlar catalyst, triple bonds can be partially hydrogenated into double bonds, whereby preferably the Z-form is produced.

The acylation of an amino group is carried out in the usual way with, for example, an acid halide or acid anhydride, optionally in the presence of a base such as dimethylaminopyridine in solvents such as methylene chloride, tetrahydrofuran or pyridine, according to the Schotten-Baumann variant in aqueous solution at weakly alkaline pH or by reaction with an anhydride in glacial acetic acid.

The introduction of the halogens chlorine, bromine, iodine or the azido group via an amino group can also be carried out, for example, according to Sandmeyer, by the diazonium salts that are formed as intermediate products with nitrites being reacted with copper(I) chloride or copper (I) bromide in the presence of the corresponding acid such as hydrochloric acid or hydrobromic acid or with potassium iodide.

If an organic nitrite is used, the halogens can be introduced into a solvent, such as, for example, dimethylformamide, e.g., by addition of methylene iodide or tetrabromomethane. The removal of the amino group can be achieved either by reaction with an organic nitrite in tetrahydrofuran or by diazotization and reductive boiling down of the diazonium salt with, for example, phosphorous acid optionally with the addition of copper(I) oxide.

The introduction of fluorine can be carried out by, for example, Balz-Schiemann reaction of the diazonium tetrafluoroborate or according to J. Fluor. Chem. 76, 1996, 59–62 by diazotization in the presence of HFxpyridine and subsequent boiling-down optionally in the presence of a fluoride ion source, such as, e.g., tetrabutylammonium fluoride.

The introduction of the azido group can be carried out after diazotization by reaction with sodium azide at room temperature.

Ether cleavages are performed according to processes that are common in the literature. In this case, a selective cleavage can be achieved also in several groups that are present in the molecule. In this case, the ether is treated with, for example, boron tribromide in solvents such as dichloromethane at temperatures of between –100° C. up to the boiling point of the solvent, preferably at –78° C. It is also possible, however, to cleave the ether by sodium thiomethylate in solvents such as dimethylformamide. The temperature can lie between room temperature and the boiling point of the solvent, preferably at 150° C.

The N- or O-alkylation of amides such as the pyrid-2-one or 2-hydroxypyridine can be carried out according to methods that are known in the literature. An N-alkylation thus can be achieved with bases such as sodium hydride or potassium carbonate in solvents such as dimethylformamide and alkylation with alkyl halides such as methyl iodide. An O-alkylation with bases such as silver carbonate in solvents such as tetrahydrofuran or toluene or preferably mixtures thereof with alkyl halides, such as methyl iodide. An O-alkylation is also obtained during conversion with trialkyloxonium tetrafluoroborate in inert solvents such as methylene chloride. Mixtures of N- and o-alkyl derivatives are obtained in the reaction with diazomethane or trimethylsilyldiazomethane in solvents such as methanol or toluene, preferably in mixtures thereof at temperatures up to the boiling point of the solvent, but preferably at room temperature. The methods make possible a selective-alkylation of the pyridone relative to the benzoic acid amide.

According to commonly used methods, such as, for example, crystallization, chromatography or salt formation, the isomer mixtures can be separated into enantiomers or E/Z-isomers.

The production of the salts is carried out in the usual way, by a solution of the compound of formula I being mixed with the equivalent amount or an excess of a base or acid, which optionally is in solution, and the precipitate being separated or the solution being worked up in the usual way.

If the production of the starting compounds is not described, the latter are known or can be produced analogously to known compounds or processes that are described here.

Also subjects of this invention are the isatoic acid derivatives of general formula V

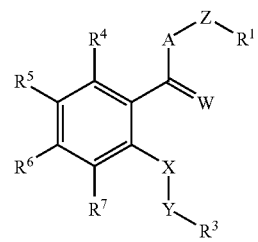

in which $R^3$–$R^7$, X, Y and W have the meanings that are described in general formula I and in which A stands for the group =$NR^2$ or oxygen, and Z and $R^1$ together form a =C=O group that is bonded to X, as well as their isomers and salts, as valuable intermediate products for the production of the compounds of general formula I according to the invention.

Especially valuable are those intermediate products of general formula V in which

| | |
|---|---|
| A and W | stand for oxygen, |
| Z and R' | together form a =C=O group that is bonded to X, |
| X | stands for the group =$NR^9$ or =N—, |
| Y | stands for the group —$CH_2$—, |
| $R^3$ | stands for pyridyl or phenyl or 1, 2, 3, 4-tetrahydronaphthyl that is substituted by hydroxy, bromine, methyl or methoxy, |
| $R^5$ and $R^6$ | stand for hydrogen, chlorine, methyl, methoxy or trifluoromethyl, |
| $R^4$ and $R^7$ | stand for hydrogen, |
| $R^9$ | stands for hydrogen, | as well as their isomers and salts.

The intermediate products are partially active on their own and can thus also be used for the production of a pharmaceutical agent for the treatment of tumors, psoriasis, arthritis, such as rheumatoid arthritis, hemangioma, angiofibroma, eye diseases, such as diabetic retinopathy, neovascular glaucoma, renal diseases, such as glomerulonephritis, diabetic nephropathy, malignant nephrosclerosis, thrombic microangiopathic syndrome, transplant rejections and glomerulopathy, fibrotic diseases, such as cirrhosis of the liver, mesangial-cell-proliferative diseases, arteriosclerosis, injuries to the nerve tissue, inhibition of the reocclusion of vessels after balloon catheter treatment, in vascular prosthetics or after mechanical devices are used to keep vessels open, such as, e.g., stents.

The examples below explain the production of the compounds according to the invention without limiting the scope of the claimed compounds to these examples.

EXAMPLE 1.0

Production of N-(4-Pyridylmethyl)-anthranilic acid methyl ester

Under nitrogen atmosphere, a mixture of 7.5 g of anthranilic acid methyl ester and 8.6 g of pyridine-4-carbaldehyde in 300 ml of methanol is mixed with 3 ml of acetic acid and stirred for 12 hours at room temperature. Then, the reaction mixture is mixed with 5.7 g of sodium cyanoborohydride (85%) and stirred for another 3 hours at room temperature. After this time, 1.14 g of sodium cyanoborohydride (85%) is added again and stirred for another 12 hours at room temperature. The reaction mixture is concentrated by evaporation. The residue is taken up in ethyl acetate and washed with saturated sodium bicarbonate solution and saturated sodium chloride solution. The dried organic phase is concentrated by evaporation, and the residue is purified with use of column chromatography on silica gel with use of hexane/ethyl acetate (1+1).

10.2 g of the title compound with a melting point of 85.6° C. is obtained.

EXAMPLE 2.0

Production of N-(3-phenylprop-1-yl)-N2-(4-pyridylmethyl)-anthranilic acid amide 242 mg of N-(4-pyridylmethyl)-anthranilic acid methyl ester is introduced into 3.5 ml of toluene, mixed with 202 mg of 3-phenylpropylamine and quickly mixed at 0° C. with 0.75 ml of a 2 molar solution of trimethylaluminum in toluene. The reaction mixture is then heated for 1 hour at room temperature and then refluxed for 1 hour. After cooling, the reaction mixture is added to saturated sodium bicarbonate solution and extracted with ethyl acetate. The organic phase is washed, dried, filtered and concentrated by evaporation in a vacuum. The residue is then recrystallized from ethyl acetate.

265 mg of the title compound with a melting point of 117.4° C. is obtained.

Produced similarly to Example 2.0 are also the following compounds:

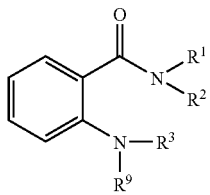

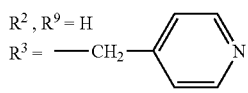

| Beispiel | $R^1$ | Schmelzpunkt ° C. |
|---|---|---|
| 2.1 | —CH$_2$—C$_6$H$_4$—Cl | 133.4 |
| 2.2 | indanyl | 152.8 |
| 2.3 | —(CH$_2$)$_2$—C$_6$H$_4$—Cl | 107.7 |
| 2.4 | —NH—C$_6$H$_4$—Cl | Öl |
| 2.5 | —N(CH$_3$)—C$_6$H$_5$ | 123–124 |
| 2.6 | —CH$_2$—thienyl | 88.1 |

-continued
| | | |
|---|---|---|
| 2.7 | —C(CH₃)₂—CH₂—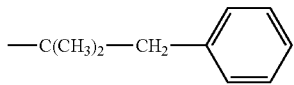 | 114.5 |
| 2.8 | 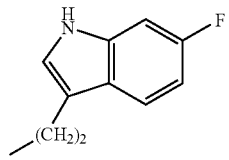 | 170.5 |
| 2.9 | 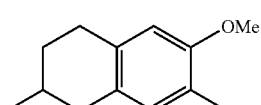 | 65.5 |
| 2.10 | —CH₂—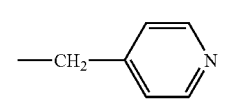 | Öl |
| 2.11 | 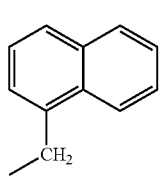 | 119 |
| 2.12 | 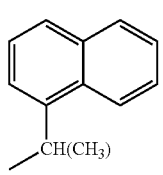 | 156.2 |
| 2.13 | 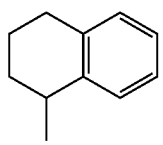 | 121.7 |
| 2.14 | —(CH₂)₃—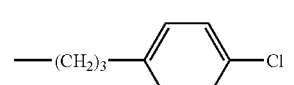—Cl | Öl |
| 2.15 | —CH(CH₃)—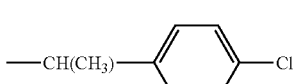—Cl | 166.4 |
| 2.16 | —CH₂—CH(CH₃)—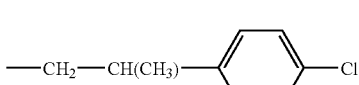—Cl | Öl |
| 2.17 | —CH(CH₃)—CH₂—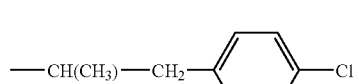—Cl | 132.9 |
| 2.18 | —CH₂—CH(CH₃)—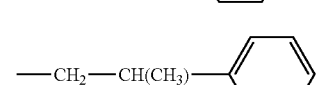 | Öl |
| 2.19 | —C(CH₃)₂—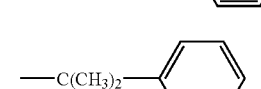 | 133.8 |

-continued
| | | |
|---|---|---|
| 2.20 | 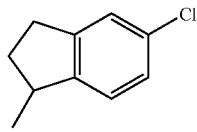 | Öl |
| 2.21 | 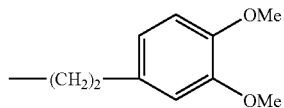 | Öl |
| 2.22 | 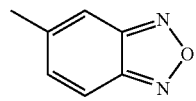 | Öl |
| 2.23 | 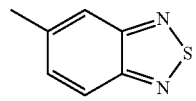 | Öl |
| 2.24 | 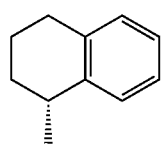 | Öl |
| 2.25 | 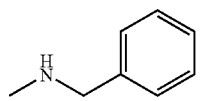 | Öl |
| 2.26 | 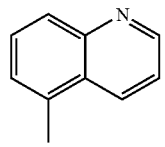 | 129.7 |
| 2.27 | 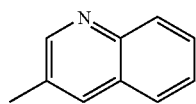 | 182.4 |
| 2.28 | 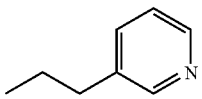 | 105–106 |
| 2.29 | 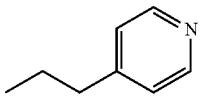 | 94–95 |
| 2.30 | 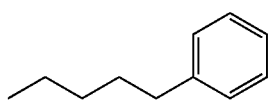 | Öl |
| 2.31 | 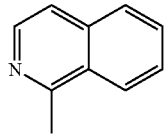 | 152.3 |

-continued
| | | |
|---|---|---|
| 2.32 | 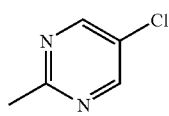 | 173–175 |
| 2.33 | 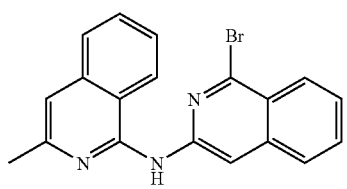 | 190–192 |
| 2.34 | 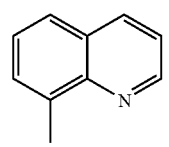 | 176.4 |
| 2.35 | 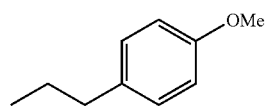 | 110–111 |
| 2.36 | 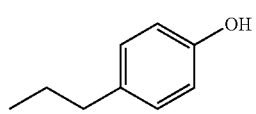 | 157–159 |
| 2.37 | 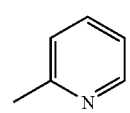 | 118–120 |
| 2.38 | 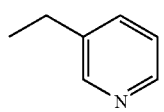 | 119–121 |
| 2.39 | 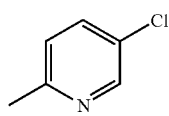 | 130–132 |
| 2.40 | 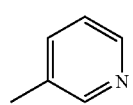 | 128–129 |
| 2.41 | 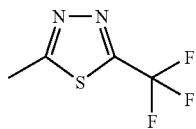 | 172–174 |
| 2.42 | 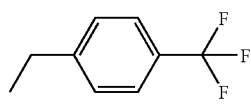 | 155–156 |
| 2.43 | 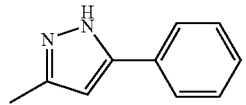 | 167 |

-continued

| | | |
|---|---|---|
| 2.44 | 4-methylcyclohexyl-phenyl | 178.8 |
| 2.45 | (R)-1-methyl-1,2,3,4-tetrahydronaphthalene | Öl |
| 2.46 | n-propylbenzene | Öl |
| 2.47 | 1-ethylisoquinoline | 140–142 |
| 2.48 | 2-ethylquinoline | 116–118 |
| 2.49 | 7-methyl-1,2,3,4-tetrahydroquinoline | 96–99 |
| 2.50 | trans-2-methyl-1-phenylcyclohexane | 169.4 |
| 2.51 | 6-methyl-2,3-dihydro-1,4-benzodioxine | 145–147 |
| 2.52 | 6-methylquinoline | 141.1 |
| 2.53 | 2-methylquinoline | 160.6 |
| 2.54 | 3-methylisoquinoline | 134.3 |
| 2.55 | 5-methylisoquinoline | Öl |

-continued
| | | |
|---|---|---|
| 2.56 | 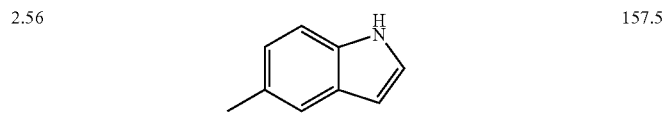 | 157.5 |
| 2.76 | 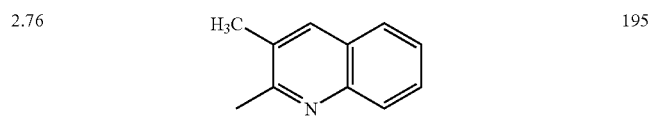 | 195 |
| 2.77 | 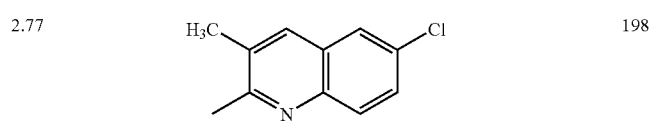 | 198 |
| 2.78 | 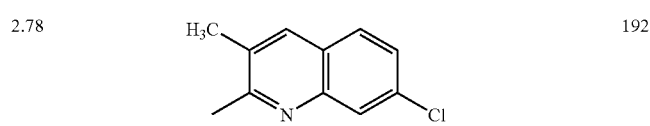 | 192 |
| 2.79 | 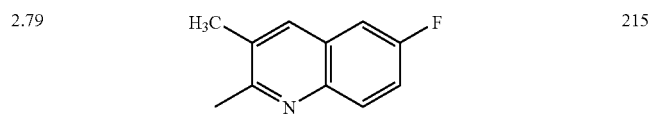 | 215 |
| 2.80 | 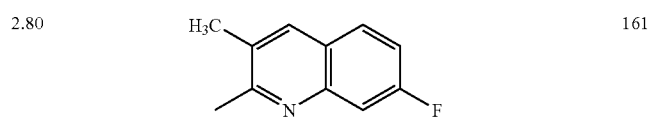 | 161 |
| 2.81 | 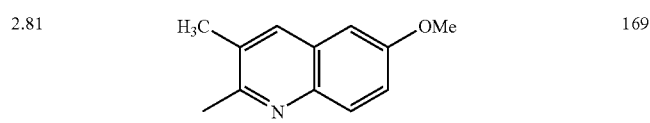 | 169 |
| 2.82 | 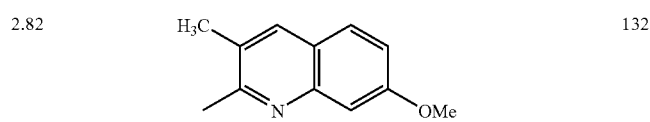 | 132 |
| 2.83 | 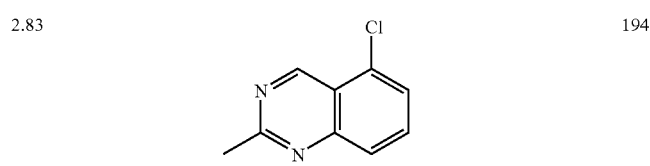 | 194 |

-continued
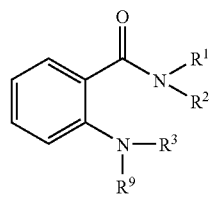
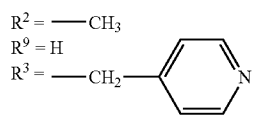
| Beispiel | R¹ | Schmelzpunkt ° C. |
|---|---|---|
| 2.57 | 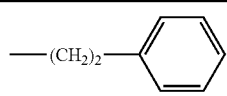 | Öl |
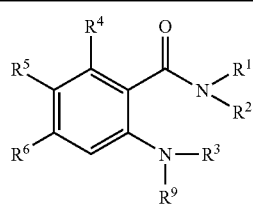
R², R⁹= H
| Beispiel | R⁶ | R⁵ | R⁴ | R³ | R¹ | Schmelzpunkt ° C. |
|---|---|---|---|---|---|---|
| 2.58 | H | Cl | H | 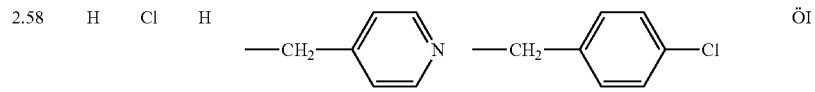 | | Öl |
| 2.59 | H | H | Cl | 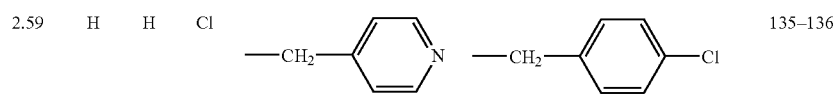 | | 135–136 |
| 2.60 | H | Cl | H | 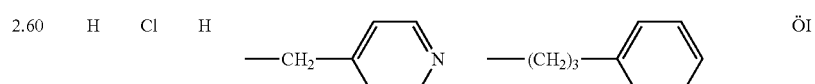 | | Öl |
| 2.61 | H | H | Cl | 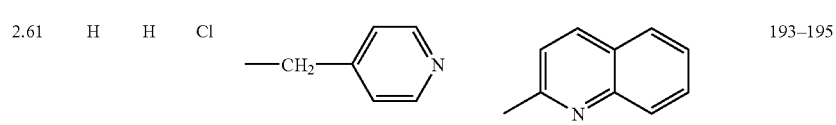 | | 193–195 |
| 2.62 | H | Cl | H | 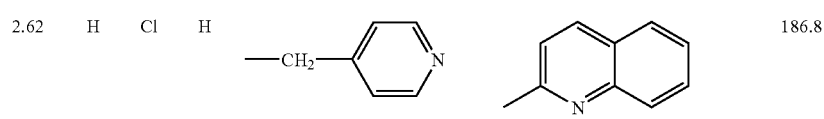 | | 186.8 |
| 2.63 | H | F | H | 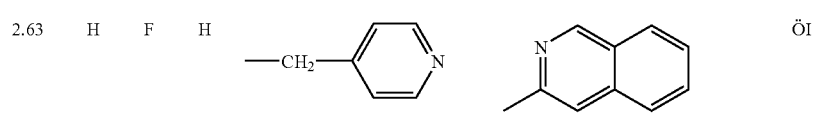 | | Öl |
| 2.64 | H | Cl | H | 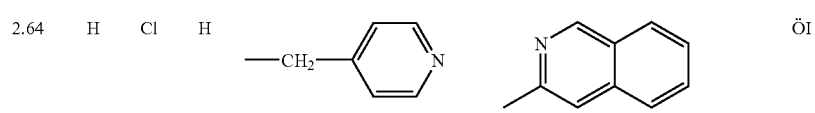 | | Öl |

-continued

| Beispiel | R⁹ | R³ | B | Schmelzpunkt ° C. |
|---|---|---|---|---|
| 2.65 | F | H | H —CH₂—(4-pyridyl) | 3-methylisoquinoline | 168.6 |
| 2.66 | H | Cl | H —CH₂—(4-pyridyl) | 3-methyl-5-phenyl-1H-pyrazole | Öl |
| 2.67 | H | F | H —CH₂—(4-pyridyl) | 3-methyl-5-phenyl-1H-pyrazole | Öl |
| 2.68 | H | Cl | H —CH₂—(4-pyridyl) | 5-chloro-2-methylpyrimidine | Öl |
| 2.69 | H | F | H —CH₂—(4-pyridyl) | 5-chloro-2-methylpyrimidine | Öl |
| 2.84 | Cl | H | H —CH₂—(4-pyridyl) | 2-methylquinoline | 165.6 |
| 2.85 | H | H | F —CH₂—(4-pyridyl) | 3-methylisoquinoline | Harz |
| 2.86 | F | F | H —CH₂—(4-pyridyl) | 3-methylisoquinoline | 206.0 |

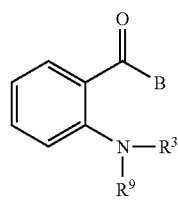

| Beispiel | R⁹ | R³ | B | Schmelzpunkt ° C. |
|---|---|---|---|---|
| 2.70 | H | —CH₂—(4-pyridyl) | 2-methyl-1,2,3,4-tetrahydroisoquinoline | Öl |
| 2.71 | H | —CH₂—(4-pyridyl) | 1-methyl-4-(4-chlorophenyl)-1,2,3,6-tetrahydropyridine | 136.8 |
| 2.72 | H | —CH₂—(4-pyridyl) | 1-methyl-1H-indazole | Öl |

| | | | |
|---|---|---|---|
| 2.73 | H | —CH₂—⟨C₆H₄⟩—OMe | 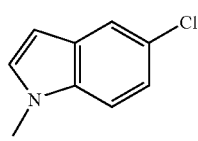 | Öl |
| 2.74 | H | —CH₂—⟨pyridyl⟩ | 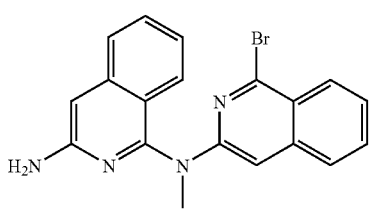 | Öl |
| 2.75 | H | —CH₂—⟨pyridyl⟩ | 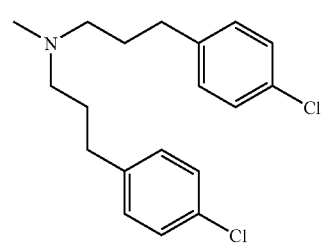 | Öl |

[Key:]
Beispiel = Example; Schmelzpunkt = Melting Point

EXAMPLE 3.0

Production of N-(4-chlorobenzyl)-N-2-(4-methoxybenzyl)anthranilamide 425 mg of N-(4-methoxybenzyl)isatoic acid anhydride is dissolved in 20 ml of tetrahydrofuran p.A., mixed with 234 mg of 4-chlorobenzylamine and refluxed for 4 hours. The reaction solution is concentrated by evaporation in a vacuum, taken up in ethyl acetate, washed, dried, filtered and concentrated by evaporation in a vacuum. The residue is recrystallized from ethyl alcohol. The title compound with a melting point of 130.5° C. is obtained.

Similarly produced are also the following compounds:

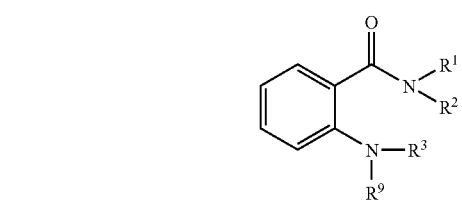

$R^2, R^9 = H$

| Beispiel | $R^3$ | $R^1$ | Schmelzpunkt ° C. |
|---|---|---|---|
| 3.1 | —CH₂—⟨C₆H₄⟩—OMe | —CH₂—⟨C₆H₄⟩—OMe | 100.7 |
| 3.2 | —CH₂—⟨C₆H₄⟩—OMe | —(CH₂)₂—⟨C₆H₄⟩—Cl | 110.5 |

[Key:]
Beispiel = Example; Schmelzpunkt = Melting Point

EXAMPLE 4.0

Production of N-[2-(4-chlorophenyl)ethyl]-N-2-(4-hydroxybenzyl) anthranilamide 71 mg of N-[2-(4-chlorophenyl)ethyl]-N-2-(4-methoxybenzyl)anthranilamide is dissolved under nitrogen atmosphere in 2 ml of absolute dimethylformamide and mixed with 76 mg of sodium thiomethylate. The reaction mixture is refluxed for 1.5 hours. After cooling, it is mixed with 30 ml of water and then extracted with ethyl acetate. The organic phase is washed, dried, filtered and evaporated to the dry state in a vacuum. The residue is chromatographed on silica gel with hexane+ethyl acetate (7+3) as an eluant.

23 mg of the title compound with a melting point of 103–105° C. is obtained.

EXAMPLE 5.0

Production of 2-[(-2-chloropyridin-4-yl)methyl]amino]-N-(isoquinolin-3-yl)benzoic acid amide 300 mg of 2-[amino]7N-(isoquinolin-3-yl)benzoic acid amide is mixed in 6 ml of methanol with 0.06 ml of glacial acetic acid and 523 mg of a 39% solution of 2-chloro-4-pyridine carbaldehyde in methylene chloride and ethyl acetate, and it is stirred for 20 hours at room temperature under argon. Then, 96 mg of sodium cyanoborohydride is added, and it is stirred for 6 hours at room temperature. After concentration by evaporation in a vacuum, the residue is taken up in 30 ml of a dilute solution of sodium bicarbonate in water and extracted with ethyl acetate. The ethyl acetate phase is washed with water, dried, filtered and concentrated by evaporation. The residue is chromatographed on silica gel with ethyl acetate as an eluant. After the corresponding fractions are combined and concentrated by evaporation, 56 mg of 2-[(−2-chloropyridin-4-yl)methyl]amino]-N-(isoquinolin-3-yl)benzoic acid amide is obtained.

Similarly produced are also the following compounds:

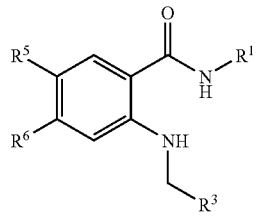

| Beispiel | $R^1$ | $R^3$ | $R^6$ | $R^5$ | Schmelzpunkt ° C. |
|---|---|---|---|---|---|
| 5.1 | isoquinolin-3-yl | 4-methyl-2-hydroxypyridin-yl | H | H | Öl |
| 5.2 | isoquinolin-3-yl | 5-methyl-2-hydroxypyridin-yl | H | H | 238.3 |
| 5.3 | isoquinolin-1-yl | 5-methyl-2-hydroxypyridin-yl | F | H | Öl |
| 5.4 | isoquinolin-3-yl | 4-methyl-2-hydroxypyridin-yl | H | F | Öl |

-continued

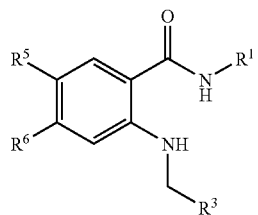

| Beispiel | R¹ | R³ | R⁶ | R⁵ | Schmelzpunkt ° C. |
|---|---|---|---|---|---|
| 5.5 | 3-methylisoquinoline | 5-methyl-2-hydroxypyridine | Cl | H | Öl |
| 5.6 | 3-methylisoquinoline | 4-methylpyrimidine | H | H | 171.8 |
| 5.7 | 2-methylquinoline | 4-methyl-2-methoxypyrimidine | H | H | Öl |
| 5.8 | 2-methylbenzothiazole | 5-methyl-2-hydroxypyridine | F | H | Öl |
| 5.9 | 5-methyl-1H-indazole | 4-methyl-2-hydroxypyridine | H | H | Öl |
| 5.10 | 6-methyl-1H-indazole | 4-methyl-2-chloropyridine | H | F | Öl |
| 5.11 | 3-methyl-5-phenyl-1H-pyrazole | 4-methyl-2-hydroxypyridine | H | H | Öl |
| 5.12 | 3-methylisoquinoline | 4-methylpyrimidine | F | H | Öl |

-continued
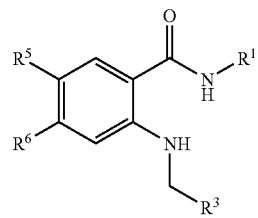
| Beispiel | R¹ | R³ | R⁶ | R⁵ | Schmelzpunkt ° C. |
|---|---|---|---|---|---|
| 5.13 | 3-methylisoquinoline | 4-methylpyrimidine | H | F | 156.1 |
| 5.14 | 3-methylisoquinoline | 5-methyl-2-pyridone | H | F | Öl |
| 5.15 | 3-methylisoquinoline | 5-methyl-2-pyridone | F | H | Öl |
| 5.16 | 5-methyl-1H-indazole | 4-methylpyrimidine | F | H | 238.6 |
| 5.17 | 5-methyl-1H-indazole | 5-methyl-2-pyridone | H | H | Öl |
| 5.18 | 6-methylcoumarin | 4-methylpyridine | H | H | Öl |
[Key:]
Beispiel = Example; Schmelzpunkt = Melting Point

EXAMPLE 6.0

Production of 2-[[(1,2-dihydro-1-methyl-2-oxopyridin-4-yl)methyl]amino]-N-(isoquinolin-3-yl)benzoic acid amide 80 mg of 2-[[(1,2-dihydro-2-oxopyridin-4'-yl)methyl]amino]-N-(isoquinolin-3-yl)benzoic acid amide in 2 ml of dimethylformamide is mixed under argon with 10 mg of sodium hydride (80%) and heated for 30 minutes to 60° C. Then, 0.015 ml of methyl iodide in 0.5 ml of dimethylformamide is added in drops and heated for 1 hour to 60° C. After cooling, the batch is added to a solution of sodium bicarbonate and extracted with ethyl acetate. The ethyl acetate phase is washed, dried and concentrated by evaporations and the residue on silica gel with methylene chloride:ethanol=97:3 as an eluant. 0.30 mg of 2-[[(1,2-dihydro-1-methyl-2-oxopyridin-4-yl)methyl]amino]-N-(isoquinolin-3-yl)benzoic acid amide is obtained.

Similarly produced are also the following compounds:

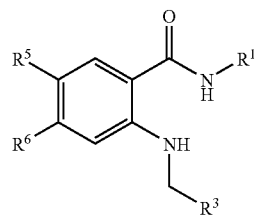

| Beispiel | $R^1$ | $R^3$ | $R^6$ | $R^5$ | Schmelzpunkt ° C. |
|---|---|---|---|---|---|
| 6.1 | isoquinolin-3-yl | 1,2-dihydro-1-methyl-2-oxopyridin-4-yl (4-Me) | H | H | Öl |
| 6.2 | isoquinolin-3-yl | 1,2-dihydro-1-methyl-2-oxopyridin-4-yl (5-Me) | H | H | Öl |
| 6.3 | 1-methyl-isoquinolin-3-yl | 1,2-dihydro-1-methyl-2-oxopyridin-4-yl (5-Me) | F | H | Öl |
| 6.4 | isoquinolin-3-yl | 1,2-dihydro-1-methyl-2-oxopyridin-4-yl (4-Me) | H | F | Öl |
| 6.5 | isoquinolin-3-yl | 1,2-dihydro-1-methyl-2-oxopyridin-4-yl (5-Me) | Cl | H | Öl |

-continued

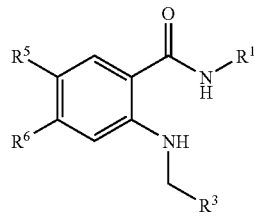

| Beispiel | R¹ | R³ | R⁶ | R⁵ | Schmelzpunkt ° C. |
|---|---|---|---|---|---|
| 6.6 | 5-methyl-1H-indazol-yl | 1,2-dihydro-1-methyl-2-oxopyridin-4-yl (5-methyl) | H | H | Öl |
| 6.7 | isoquinolin-3-yl | 1,2-dihydro-1-methyl-2-oxopyridin-4-yl (5-methyl) | H | H | Öl |

[Key:]
Beispiel = Example; Schmelzpunkt = Melting Point

EXAMPLE 7.0

Production of 2-[(−2-methoxypyridin-4-yl)methyl]amino]-N-(isoquinolin-3-yl)benzoic acid amide and 2-[[(1,2-dihydro-1-methyl-2-oxopyridin-4-yl)methyl]amino]-N-(isoquinolin-3-yl)benzoic acid amide 130 mg of 2-[[(1,2-dihydro-2-oxopyridin-4-yl)methyl]amino]-N-(isoquinolin-3-yl)benzoic acid amide is introduced into 4 ml of a mixture that consists of toluene:methanol=1:3.5 and mixed with 0.2 ml of a 2-molar solution of trimethylsilyldlazomethane in hexane and stirred for 8 hours at room temperature. After repeated addition of 0.2 ml of trimethylsilyldiazomethane solution and 1 hour of stirring, the batch is evaporated to the dry state and chromatographed on silica gel with methylene chloride:ethanol=97:3 as an eluant. 20 mg of 2-[(−2-methoxypyridin-4-yl)methyl]amino]-N-(isoquinolin-3-yl)benzic acid amide and 10 mg of 2-[[(1,2-dihydro-1-methyl-2-oxopyridin-4-yl)methyl]amino]-N-(isoquinolin-3-yl)-benzoic acid amide are obtained.

Similarly produced are also the following compounds:

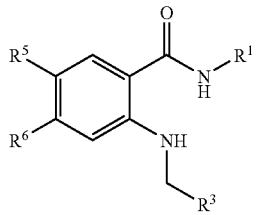

| Beispiel | R¹ | R³ | R⁶ | R⁵ | Schmelzpunkt ° C. |
|---|---|---|---|---|---|
| 7.1 | isoquinolin-3-yl | 2-methoxy-4-methylpyridin-4-yl | H | H | Öl |

-continued
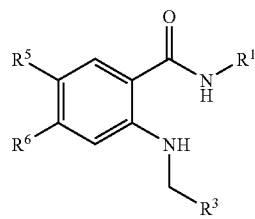
| Beispiel | R¹ | R³ | R⁶ | R⁵ | Schmelzpunkt ° C. |
|---|---|---|---|---|---|
| 7.2 | isoquinolin-3-yl | 6-methoxypyridin-3-yl | H | H | Öl |
| 7.3 | quinolin-2-yl | 2-methoxypyridin-4-yl | F | H | Öl |
| 7.4 | 5-chloropyrimidin-2-yl | 6-methoxypyridin-3-yl | H | F | Öl |
| 7.5 | isoquinolin-3-yl | 6-methoxypyridin-3-yl | Cl | H | Öl |
| 7.6 | 1H-indazol-5-yl | 6-methoxypyridin-3-yl | H | H | Öl |
| 7.7 | isoquinolin-3-yl | 6-methoxypyridin-3-yl | H | H | Öl |
[Key:]
Beispiel = Example; Schmelzpunkt = Melting Point

EXAMPLE 8.0

Production of N-(indazol-5-yl) N2-(4-pyridylmethyl)-anthranilic acid amide 228 mg of N-(4-pyridylmethyl)-anthranilic acid is introduced into 10 ml of dimethylformamide under argon and in a moisture-free environment. 266 mg of 5-aminoindazole, 0.27 ml of methylmorpholine and 456 mg of O-(7-azabenzotriazol-1-yl)-N,N,N',N'-tetramethyluronium hexafluorophosphate (HATU) are added. The mixture is then stirred for 4 hours at room temperature. It is then mixed with dilute sodium bicarbonate solution and extracted three times with ethyl acetate. The combined organic phases are washed with water, dried, filtered and concentrated by evaporation in a vacuum. The residue is chromatographed on silica gel with ethyl acetate as an eluant.

By absorptive precipitation in acetone, 245 mg of the title compound with a melting point of 209.8° C. is obtained.

Similarly produced are also the following compounds:

| Beispiel | R¹ | R⁶ | R⁵ | Schmelzpunkt ° C. |
|---|---|---|---|---|
| 8.1 | (2-methylisoquinolinyl) | Cl | H | Öl |
| 8.2 | (2-methylbenzimidazolyl) | H | H | 206 |
| 8.3 | (2-methylbenzothiazolyl) | F | H | Öl |
| 8.4 | (6-methylbenzothiazolyl) | H | F | 58.7 |
| 8.5 | (5-methylindazolyl) | Cl | H | Öl |

-continued

| Beispiel | R¹ | R⁶ | R⁵ | Schmelzpunkt ° C. |
|---|---|---|---|---|
| 8.6 | 6-methyl-1H-indazol-yl | F | H | Öl |
| 8.7 | 5,6-dimethyl-1H-benzimidazol-2-yl | H | H | 211.7 |
| 8.8 | 6-methylbenzothiazol-2-yl | H | H | 140.4 |
| 8.9 | 6-trifluoromethoxy-benzothiazol-2-yl | H | H | 188.5 |
| 8.10 | 6-methyl-1H-indazol-yl | H | H | 258.2 |
| 8.11 | 4-methylpyridin-yl | H | H | 152.6 |
| 8.12 | 1,2-dimethyl-1H-benzimidazol-yl | H | H | 199.7 |
| 8.13 | 6-chloro-benzothiazol-2-yl | H | H | 178.3 |
| 8.14 | 6-methyl-1H-benzimidazol-yl | H | H | 243 |

-continued
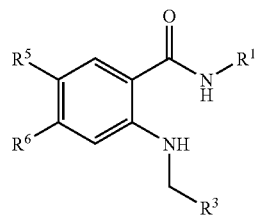
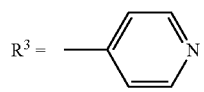
| Beispiel | R¹ | R⁶ | R⁵ | Schmelzpunkt ° C. |
|---|---|---|---|---|
| 8.15 | 5-methyl-1H-benzotriazole | H | H | Öl |
| 8.16 | 2-methyl-6-fluoro-benzothiazole | H | H | 230.4 |
| 8.17 | 2-methyl-4-chloro-benzothiazole | H | H | Öl |
| 8.18 | 2-methyl-benzothiazole | H | Cl | 235–236 |
| 8.19 | 5-methyl-1H-indazole | H | F | 236 |
| 8.20 | 5-methyl-1H-indazole | H | Cl | 228.1 |
| 8.21 | 2-methyl-benzothiazole | H | H | Öl |
| 8.22 | 2-methyl-benzothiazole | H | F | 197.6 |
| 8.23 | 6-methyl-benzothiazole | H | Cl | 59.1 |
[Key:]
Beispiel = Example; Schmelzpunkt = Melting Point The following example explains the production of the intermediate products according to the invention, without limiting the invention to these examples.

EXAMPLE 9.0

Production of N-(4-methoxybenzyl)isatoic acid anhydride as an intermediate product for the production of the end products according to the invention Under nitrogen atmosphere, a solution that consists of 5 g of isatoic acid anhydride and 100 ml of N,N-dimethylacetamide is cooled in an ice bath and mixed in portions with 1.35 g of sodium hydride (oil~60%). The reaction mixture is then stirred for 30 minutes at room temperature and for another 30 minutes at a bath temperature of 60° C. After cooling to room temperature, 5 ml of 4-methoxybenzaldehyde is added in drops while being stirred, and it is stirred overnight at room temperature. The reaction mixture is concentrated by evaporation in a vacuum and poured onto 100 ml of ice/water. The precipitate is separated, taken up in 50 ml of methylene chloride, washed, dried, filtered and concentrated by evaporation in a vacuum. The residue is recrystallized from alcohol.

3.4 g of the title compound with a melting point of 143° C. is obtained.

Similarly produced are also the following compounds:

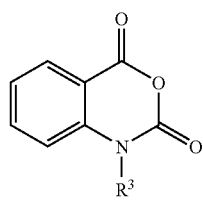

| Beispiel | R³ | Schmelzpunkt ° C. |
|---|---|---|
| 9.1 | —CH₂—⟨phenyl⟩—Br | Öl |
| 9.2 | —CH₂—⟨phenyl⟩—CH₃ | Öl |

[Key:]
Beispiel = Example; Schmelzpunkt = Melting Point

EXAMPLE 10.0

Production of N-(4-pyridylmethyl)-anthranilic acid as an intermediate product for the production of the end products according to the invention 2 g of N-(4-pyridylmethyl)-anthranilic acid methyl ester is dissolved in 15 ml of methanol, mixed with 16 ml of 1N sodium hydroxide solution and refluxed for 1 hour. After cooling, the methanol is distilled off under vacuum, and the residue is mixed with 20 ml of water and 20 ml of 1N citric acid solution. The crystals are suctioned off, washed with water and dried.

1.7 g of the title compound with a melting point of 208.0° C. is obtained.

EXAMPLE 11.0

Production of N-(indazol-5-yl)-5-chloroanthranilic acid amide as an intermediate product for the production of the end products according to the invention 171 mg of 5-chloroanthranilic acid is introduced into 10 ml of dimethylformamide under argon and in a moisture-free environment and mixed in succession with 253 mg of N-methylmorpholine, 266 mg of 5-aminoindazole and 456 mg of O-(7-azabenzotriazol-1-yl)-N,N,N',N'-tetramethyluronium hexafluorophosphate (HATU) and stirred for 4 hours at room temperature. After standing overnight, it is mixed with 50 ml of water and extracted with 30 ml of ethyl acetate. The organic phase is washed with water, dried, filtered and concentrated by evaporation. The residue is chromatographed on silica gel with ethyl acetate as an eluant. 266 mg of N-(indazol-5-yl)-5-chloroanthranilic acid amide is obtained.

The following sample applications explain the biological action and use of the compounds according to the invention without limiting the latter to the examples.

Solutions Required for the Tests
Stock solutions
Stock solution A: 3 mmol of ATP in water, pH 7.0 (−70° C.)
Stock solution B: g-0.33P-ATP 1 mCi/100 µl
Stock solution C: poly-(Glu4Tyr) 10 mg/ml in water Solution for Dilutions
Substrate solvent: 10 mmol of DTT, 10 mmol of manganese chloride, 100 mmol of magnesium chloride
Enzyme solution: 120 mmol of tris/HCl, pH 7.5, 10 µm of sodium vanadium oxide Sample Application 1
Inhibition of the KDR- and FLT-1 kinase activity in the presence of the compounds according to the invention In a microtiter plate (without protein binding) that tapers to a point, 10 µl of substrate mixture (10 µl of vol of ATP stock solution A+25 µCi of g-33P-ATP (about 2.5 µl of stock solution B)+30 µl of poly-(Glu4Tyr) stock solution C+1.21 ml of substrate solvent), 10 µl of inhibitor solution (substances that correspond to the dilutions, as a control 3% DMSO in substrate solvent), and 10 µl of enzyme solution (11.25 µg of enzyme stock solution (KDR or FLT-1 kinase) is diluted at 4° C. in 1.25 ml of enzyme solution) are added. It is thoroughly mixed and incubated for 10 minutes at room temperature. Then, 10 µl of stop solution (250 mmol of EDTA, pH 7.0) is added, mixed, and 10 µl of the solution is transferred to a P 81 phosphocellulose filter. Then, it is washed several times in 0.01 M phosphoric acid. The filter paper is dried, coated with Meltilex and measured in a microbeta counter.

The IC50 values are determined from the inhibitor concentration, which is necessary to inhibit the phosphate incorporation to 50% of the uninhibited incorporation after removal of the blank reading (EDTA-stopped reaction).

The results of kinase-inhibition IC50 in µmol are depicted in the following table:

| Beispiel-Nr. | VEGFR I (FLT) | VEGFR II (KDR) |
|---|---|---|
| 2.0 | 0.05 | 0.05 |
| 2.1 | 0.01 | 0.3 |
| 2.2 | 0.1 | 0.5 |

| Beispiel-Nr. | VEGFR I (FLT) | VEGFR II (KDR) |
|---|---|---|
| 2.3 | 0.02 | 0.02 |
| 2.4 | 0.02 | 0.1 |
| 2.5 | 1 | 10 |
| 2.6 | 0.2 | 2 |
| 2.8 | 0.5 | 0.1 |
| 2.9 | 5 | 1 |
| 2.10 | 3 | 10 |
| 2.11 | 0.02 | 0.2 |
| 2.12 | 0.7 | 3 |
| 2.13 | 0.7 | 3 |
| 2.14 | 0.5 | 0.3 |
| 2.15 | 1.0 | KH |
| 2.16 | 0.1 | 0.2 |
| 2.17 | 0.4 | 0.5 |
| 2.18 | 0.3 | 0.5 |
| 2.19 | >10 | >10 |
| 2.20 | 4 | KH |
| 2.21 | 2 | 0.3 |
| 2.23 | 0.02 | 0.67 |
| 2.24 | 0.5 | >1 |
| 2.25 | 0.3 | 0.2 |
| 2.26 | 0.2 | 0.2 |
| 2.27 | 0.02 | 0.02 |
| 2.28 | 1 | 2 |
| 2.29 | 2 | 3 |
| 2.30 | 0.005 | 0.02 |
| 2.31 | 0.1 | 0.27 |
| 2.32 | 0.02 | 0.02 |
| 2.33 | 1 | 2 |
| 2.34 | 2 | 0.1 |
| 2.35 | 0.098 | 0.02 |
| 2.36 | 0.05 | 0.2 |
| 2.37 | 0.2 | |
| 2.38 | 7 | 0.2 |
| 2.39 | 0.05 | 0.03 |
| 2.40 | 0.5 | |
| 2.41 | 1 | 0.3 |
| 2.42 | 0.5 | 0.1 |
| 2.43 | 0.02 | 0.05 |
| 2.44 | 0.3 | 0.2 |
| 2.45 | 0.1 | 1 |
| 2.46 | 0.04 | 0.05 |
| 2.47 | 0.02 | 1 |
| 2.48 | 0.1 | 0.5 |
| 2.49 | 0.08 | 0.05 |
| 2.50 | KH | KH |
| 2.51 | | |
| 2.52 | 0.05 | |
| 2.53 | 0.02 | 0.02 |
| 2.54 | 0.02 | 0.005 |
| 2.55 | 0.3 | 0.2 |
| 2.56 | 0.04 | 0.02 |
| 2.57 | KH | KH |
| 2.58 | 0.5 | 5 |
| 2.59 | 50 | KH |
| 2.60 | 0.5 | 0.7 |
| 2.61 | 10 | 10 |
| 2.63 | | 0.0003 |
| 2.64 | 0.04 | 0.04 |
| 2.65 | | 0.0002 |
| 2.74 | 1 | KH |
| 2.75 | 0.3 | 5 |
| 3.0 | KH | 3.0 |
| 3.2 | 2.0 | 2.0 |
| 4.0 | 0.5 | 0.2 |
| 8.0 | 0.04 | 0.04 |
| 8.2 | 0.2 | 0.2 |
| 8.3 | 0.05 | 0.04 |
| 8.8 | 0.05 | 0.02 |
| 8.9 | 0.5 | 0.5 |
| 8.10 | 0.02 | 0.02 |
| 8.11 | 0.2 | 1 |
| 8.12 | 0.2 | 0.1 |
| 8.13 | 0.5 | 0.5 |
| 8.14 | 0.5 | 0.2 |
| 8.15 | 0.2 | 0.2 |
| 8.16 | 0.2 | 0.3 |
| 8.17 | | 0.05 |
| 8.18 | | 0.05 |

[Key:]
Beispiel-Nr. = Example No.
KH = keine Hemmung = No inhibition

The invention claimed is:
1. A compound of formula I

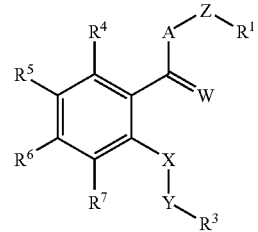

in which
A stands for the group =NR$^2$,
W stands for oxygen,
Z stands for the group

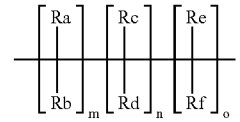

m, n and o stand for 0–3,
R$_a$, R$_b$, R$_c$, R$_d$, R$_e$, R$_f$, independently of one another, stand for hydrogen, C$_{1-4}$ alkyl or the group =NR$^{10}$, and/or R$_a$ and/or R$_b$ can form a bond with R$_e$ and/or R$_d$ or R$_c$ can form a bond with R$_e$ and/or R$_f$ or up to two of radicals R$_a$–R$_f$ form a bridge of no more than 3 C-atoms and said bridge is connected to R$^1$ or R$^2$,
X stands for the group =NR$^9$ or =N—,
Y stands for the group —(CH$_2$)$_p$,
p stands for 1–4,
R$^1$ stands for naphthyl, biphenyl, phenyl, thiophenyl, furanyl, oxazolyl, thiazolyl, imidazolyl, pyrazolyl, pyridyl, pyrimidinyl, triazinyl, quinolinyl or isoquinolinyl that is unsubstituted or substituted in one or more places with halogen, C$_{1-6}$ alkyl or C$_{1-4}$-alkoxy, hydroxy, nitro, cyano or C$_{1-6}$-alkyl or C$_{1-6}$-alkoxy that is substituted in one or more places with halogen; or 5-chloro-2,3-dihydroindenyl, 2,3-dihydroindenyl, thienyl, 6-fluoro-1H-indol-3-yl, 1,2,3,4-tetrahydronaphthyl, benzo-1,2,5-oxadiazole, 6,7-dimethoxy-1,2,3,4-tetrahydro-2-naphthyl or for one of the groups

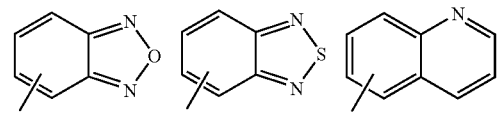

-continued

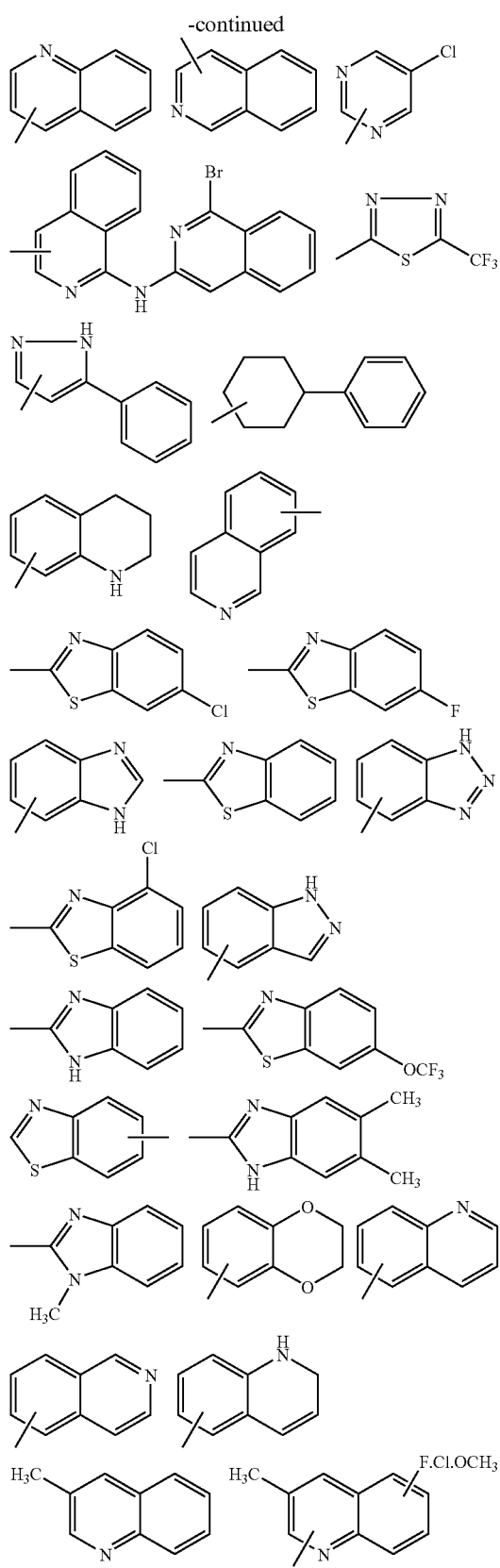

wherein an aryl group is not directly bonded to =NR² in the meaning of A,

R² stands for hydrogen or C₁₋₆ alkyl or with Rₐ–R_f from Z, or to R¹, forms a bridge with up to 3 ring members, R³ stands for monocyclic or bicyclic aryl or heteroaryl that is unsubstituted or optionally substituted in one or more places with halogen, C₁₋₆ alkyl, C₁₋₆ alkoxy or hydroxy, wherein aryl is not phenyl, R⁴, R⁵, R⁶, and R⁷, independently of one another, stand for hydrogen, halogen, or C₁₋₆ alkoxy, C₁₋₆ alkyl or C₁₋₆ carboxylalkyl that is unsubstituted or optionally substituted in one or more places with halogen, or R⁵ and R⁶ together form the group

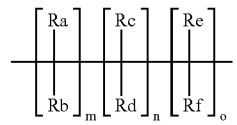

R⁸, R⁹, and R¹⁰, independently of one another, stand for hydrogen or C₁₋₆ alkyl, or an isomer or, pharmaceutically acceptable salt thereof.

2. A compound of I according to claim 1 in which

A stands for the group =NR²,

W stands for oxygen, sulfur, two hydrogen atoms or the group =NR⁸,

Z stands for the group =NR¹⁰, =N— or —N(R¹⁰)—(CH₂)_q—, branched or unbranced C₁₋₆ alkyl or the group $$\left[\begin{array}{c} R_a \\ | \\ R_b \end{array}\right]_m \left[\begin{array}{c} R_c \\ | \\ R_d \end{array}\right]_n \left[\begin{array}{c} R_e \\ | \\ R_f \end{array}\right]_o$$

m, n, and o stand for 0–3, q stands for 1–6,

Rₐ, R_b, R_c, R_d, R_e and R_f, independently of one another, stand for hydrogen, C₁₋₄ alkyl or the group =NR¹⁰

X stands for the group =NR⁹ or =N—,

Y stands for the group —(CH₂)_p, p stands for 1–4,

R¹ stands for phenyl, pyridyl, 5-chloro-2,3-dihydroindenyl,2,3-dihydroindenyl, thienyl, 6-fluoro-1H-indol-3-yl, naphthyl, 1,2,3,4-tetrahydronaphthyl, benzo-1,2,5-oxadiazole, 6,7-dimethoxy-1,2,3,4-tetrahydro-2-naphthyl or for phenyl or pyridyl that is substituted in one or more places with C₁–C₄ alkyl, C₁–C₄ alkoxy, hydroxy, halogen, or trifluoromethyl, or for the group

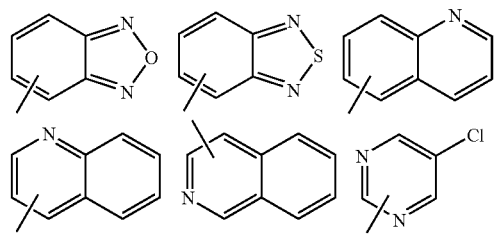

-continued

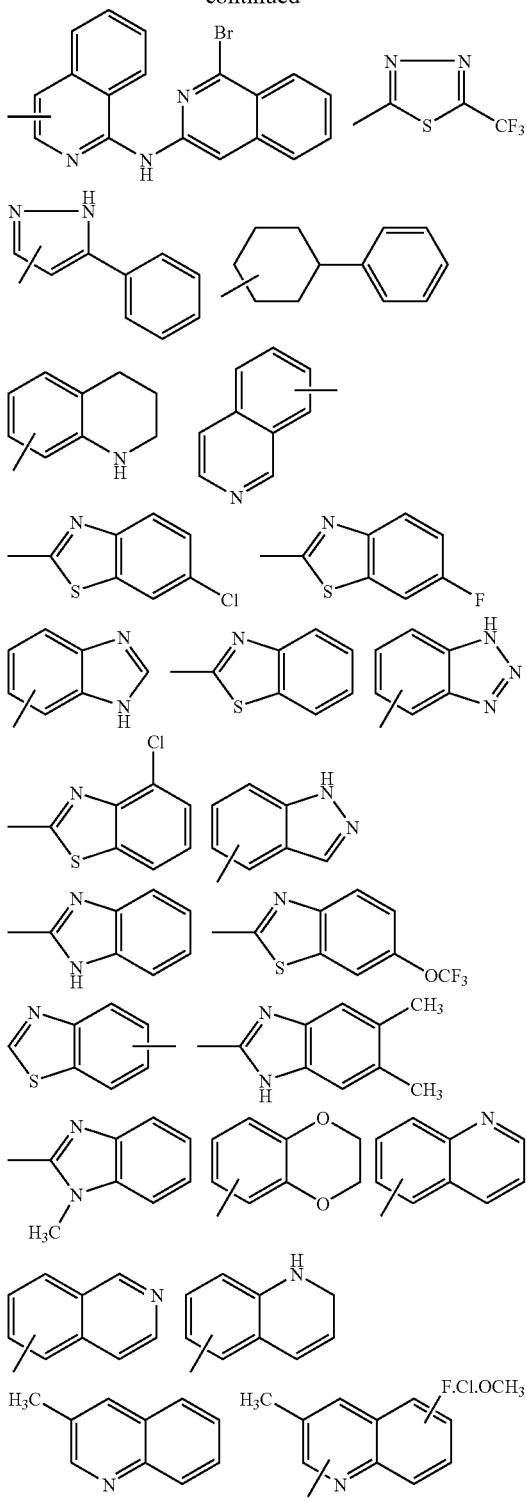

wherein an aryl group is not directly bonded to the =NR² group in the meaning of A R² stands for hydrogen or $C_{1-6}$ alkyl or with $R_a$–$R_f$ from Z, or to R¹, forms a bridge with up to 3 ring members, R³ stands for monocyclic or bicyclic heteroaryl that is one or more places with halogen, $C_{1-6}$ alkyl, $C_{1-6}$ alkoxy or hydroxy, R⁴, R⁵, R⁶, and R⁷, independently of one another, stand for hydrogen, halogen or $C_{1-6}$ alkoxy or $C_{1-6}$ alkyl that is unsubstituted or optionally substituted in one or more places with halogen, or R⁵ and R⁶ together form the group

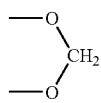

R⁸, R⁹ and R¹⁰, independently of one another, stand for hydrogen or $C_{1-6}$ alkyl, or an isomer or pharmaceutically acceptable salt thereof.

3. A compound of formula I according to claim 1, in which

A stands for the group =NR²,

W stands for oxygen, sulfur or two hydrogen atoms,

Z stands for the group =NR¹⁰, =N, —N(R¹⁰)—(CH₂)$_q$— or the group

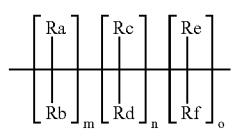

m, n and 0 stand for 0–3, q stands for 1–6, $R_a$, $R_b$, $R_c$, $R_d$, $R_e$, $R_f$ independently of one another, stand for hydrogen or methyl or the group =NR¹⁰, X stands for the group =NR⁹ or =N—, Y stands for the group —CH₂—, R¹ stands for phenyl, pyridyl, p-chlorophenyl, p-methylphenyl, p-methoxyphenyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole, 6,7-dimethoxy-1,2,3,4-tetrahydro-2-naphthyl, or for phenyl or pyridyl that is substituted in one or more places with $C_1$–$C_4$ alkyl, $C_1$–$C_4$ alkoxy, hydroxy, halogen, trifluoromethyl, or for the group

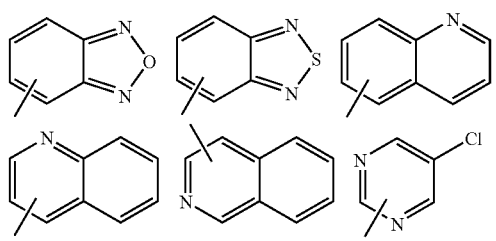

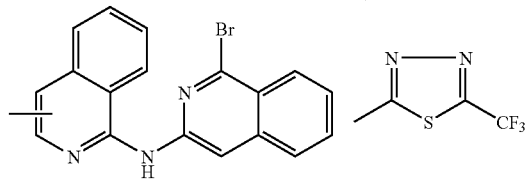

-continued

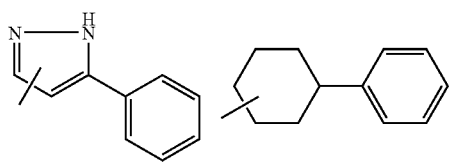
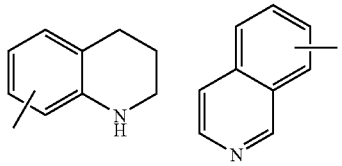
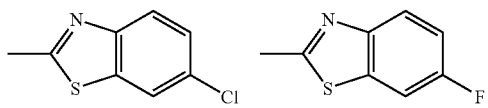
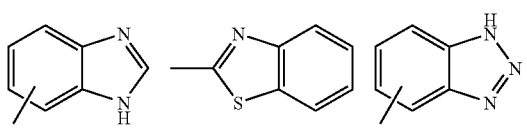
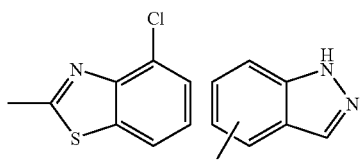
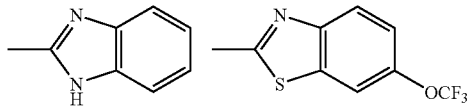
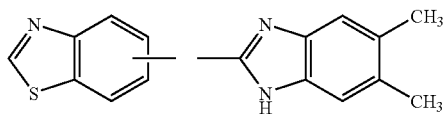
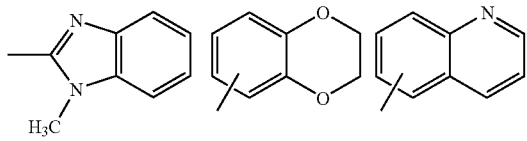
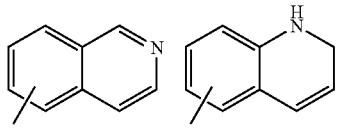
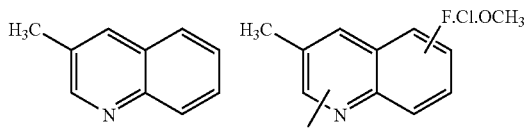

wherein an aryl group is not directly bonded to the =NR² group in the meaning of A, $R^2$ stands for hydrogen or methyl, $R^3$ stands for pyridyl, or 1,2,3,4-tetrahydronaphthyl that is substituted by hydroxy, halogen, methyl or methoxy, or for the group

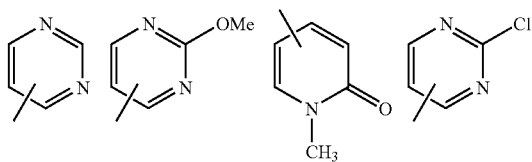

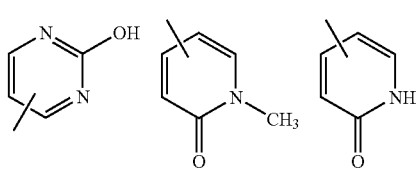

$R^5$ and $R^6$, independently of one another, stand for hydrogen, halogen, methyl, methoxy or trifluoromethyl, $R^4$ and $R^7$, independently of one another, stand for hydrogen, $R^9$ stands for hydrogen, $R^{10}$ stands for hydrogen or methyl, or an isomer or pharmaceutically acceptable salt thereof.

4. A compound of formula I according to claim 1, in which

A stands for the group =NR²,

W stands for oxygen,

Z stands for the group =NR¹⁰, =N—, —N(R¹⁰)—(CH₂)$_q$— or the group $$\left[\begin{array}{c}R_a\\|\\R_b\end{array}\right]_m\left[\begin{array}{c}R_c\\|\\R_d\end{array}\right]_n\left[\begin{array}{c}R_e\\|\\R_f\end{array}\right]_o$$

m, n and o stand for 0–3, q stands for 1–6, $R_a, R_b, R_c, R_d, R_e, R_f$, independently of one another, stand for hydrogen or methyl or the group =NR¹⁰, X stands for the group =NR⁹ or =N—, Y stands for the group —CH₂—, $R^1$ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-napthyl or for a phenyl or pyridyl that is substituted in one or places with $C_1$–$C_4$ alkyl, $C_1$–$C_4$ alkoxy, hydroxy, halogen, or trifluoromethyl, or for the group

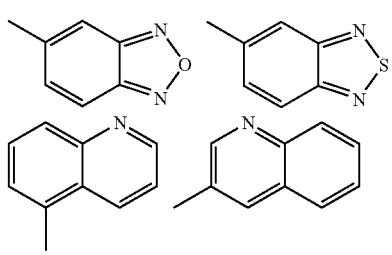

-continued

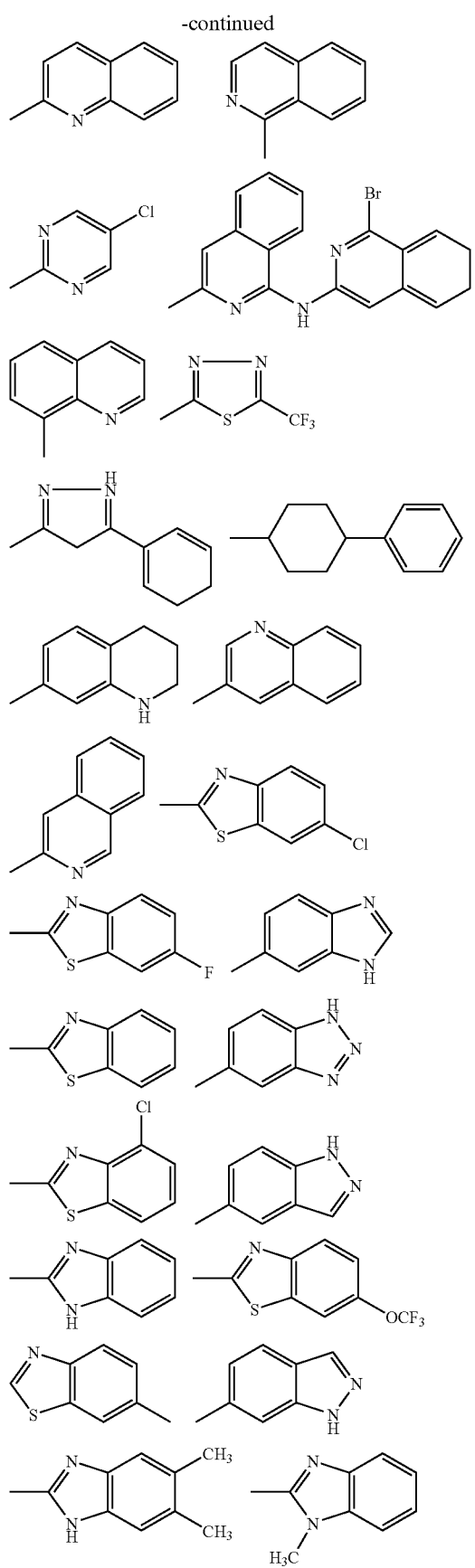

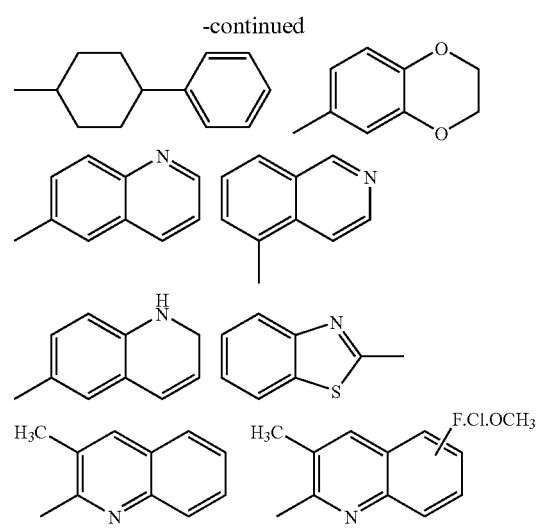

wherein an aryl group is not directly bonded to the =NR² group in the meaning of A, R² stands for hydrogen or methyl, R³ stands for pyridyl or for pyridyl or 1,2,3,4-tetrahydronaphthyl that is substituted in one or more places with hydroxy, halogen, methyl or methoxy, or for the group

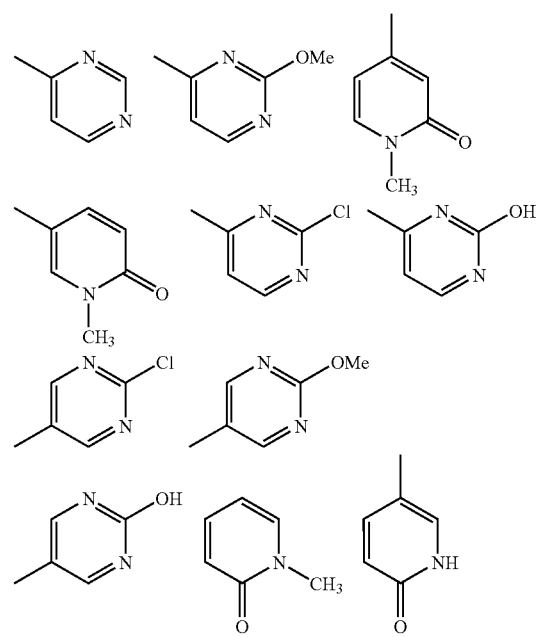

R⁵ and R⁶, independently of one another, stand for hydrogen, halogen, methyl, methoxy, or trifluoromethyl, R⁴ and R⁷, independently of one another, stand for hydrogen and halogen, R⁹ stands for hydrogen, R¹⁰ stands for hydrogen or methyl, or an isomer or pharmaceutically acceptable salt thereof.

5. A compound of formula I according to claim 1, in which

A stands for the group =NR$^2$,

W stands for sulfur,

Z stands for the group =NR$^{10}$, =N—, —N(R$^{10}$)—(CH$_2$)$_q$— or the group $$\left[\begin{array}{c}R_a \\ | \\ | \\ R_b\end{array}\right]_m \left[\begin{array}{c}R_c \\ | \\ | \\ R_d\end{array}\right]_n \left[\begin{array}{c}R_e \\ | \\ | \\ R_f\end{array}\right]_o$$

m, n and o stand for 0–3, q stands for 1–6,

R$_a$, R$_b$, R$_c$, R$_d$, R$_e$, R$_f$, independently of one another, stand for hydrogen or methyl or X stands for the group =NR$^9$ or =N—, Y stands for the group —CH$_2$—, R$^1$ stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-naphthyl or for phenyl or pyridyl that is substituted in one or more places with C$_1$–C$_4$ alkyl, C$_1$–C$_4$ alkoxy, hydroxy, halogen, or trifluoromethyl, or for the group wherein an aryl group is not bonded directly to the =NR$^2$ group in the meaning of A, R$^2$ stands for hydrogen or methyl, R$^3$ stands for pyridyl or for pyridyl or 1,2,3,4-tetrahydronaphthyl that is substituted in one or more places with hydroxy, halogen, methyl or methoxy, or for the group

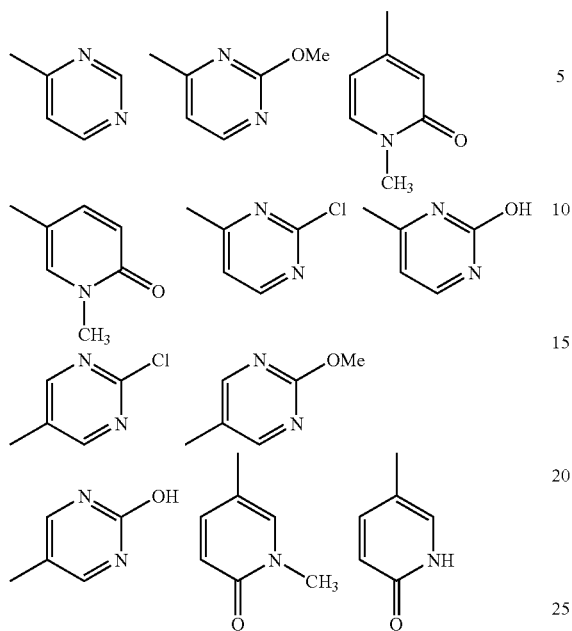

R[5] and R[6], independently of one another, stand for hydrogen, halogen, methyl, methoxy or trifluoromethyl, R[4] and R[7], independently of one another, stand for hydrogen and halogen, R[9] stands for hydrogen, R[10] stands for hydrogen or methyl, or an isomer or pharmaceutically acceptable salt thereof.

6. A compound of formula I according to claim 1, in which

A stands for the group =NR[2],

W stands for two hydrogen atoms,

Z stands for the group =NR[10], =N—, —N(R[10])—(CH$_2$)$_q$— or the group

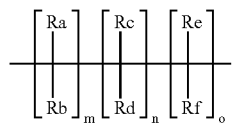

m, n and o stand for 0–3, q stands for 1–6, $R_a$, $R_b$, $R_c$, $R_d$, $R_e$, $R_f$ independently of one another, stand for hydrogen or methyl or the group =NR[10], X stands for the group =NR[9] or =N—, Y stands for the group —CH$_2$—, R[1] stands for phenyl, pyridyl, 5-chloro-2,3-dihydroindenyl, 2,3-dihydroindenyl, thienyl, 6-fluoro-1H-indol-3-yl, naphthyl, 1,2,3,4-tetrahydronaphthyl, benzo-1,2,5-oxadiazole or 6,7-dimethoxy-1,2,3,4-tetrahydro-2-naphthyl or for a phenyl or pyridyl that is substituted in one or more places with C$_1$–C$_4$ alkyl, C$_1$–C$_4$ alkoxy, hydroxy, halogen, or trifluoromethyl, or for the group

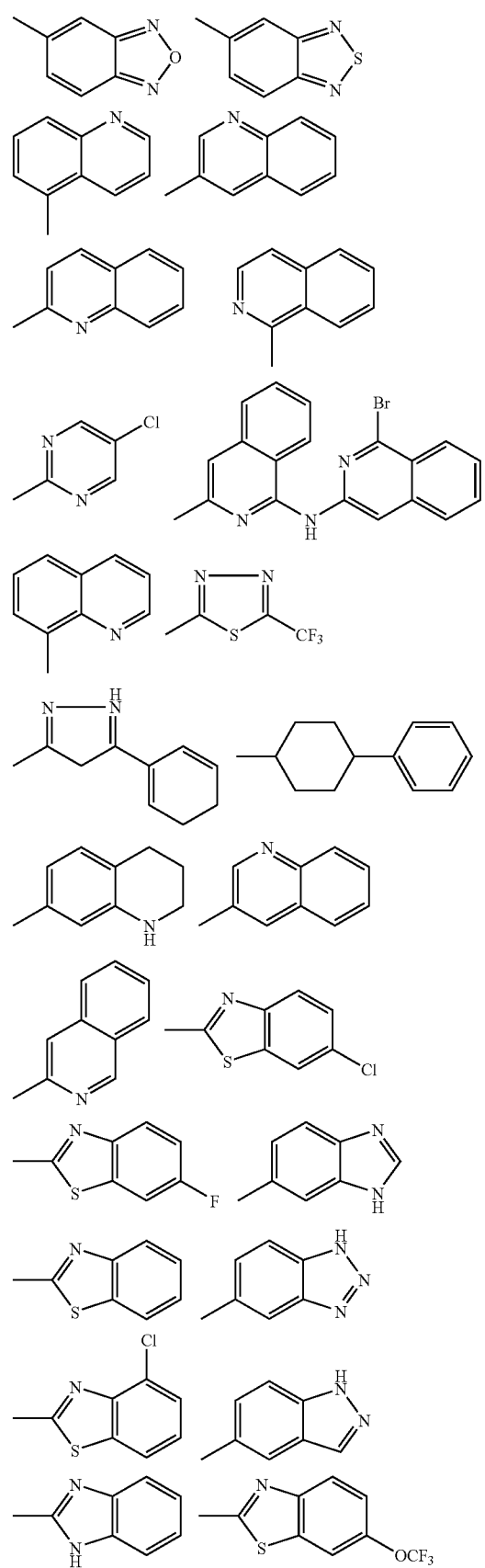

-continued

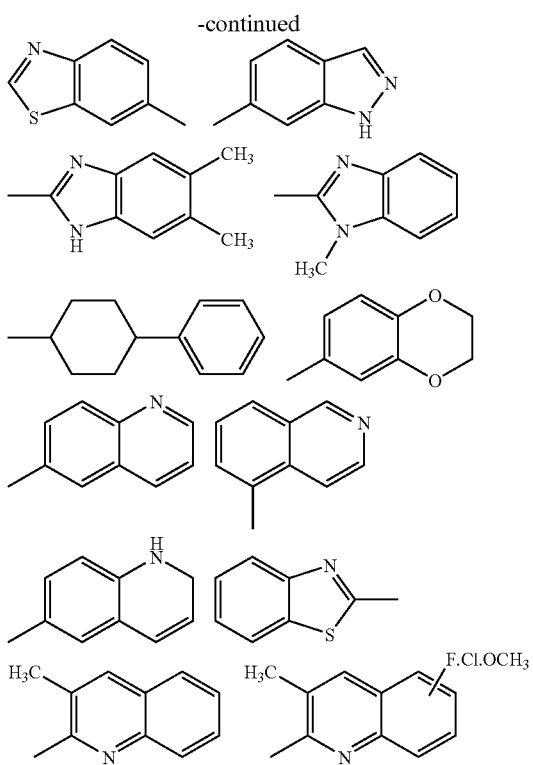

wherein an aryl group is not directly bonded to the =NR² group in the meaning of A, R² stands for hydrogen or methyl, R³ stands for pyridyl or for pyridyl or 1,2,3,4-tetrahydronaphthyl that is substituted in one or more places with hydroxy, halogen, methyl or methoxy, or for the group

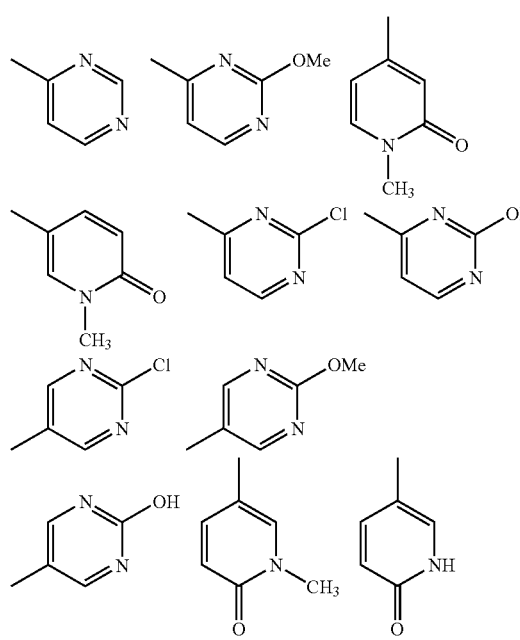

R⁴ and R⁷, independently of one another, stand for hydrogen, halogen, methyl, methoxy or trifluoromethyl, R⁵ and R⁶, independently of one another, stand for hydrogen and halogen, R⁹ stands for hydrogen, R¹⁰ stands for hydrogen or methyl, or an isomer or pharmaceutically acceptable salt thereof.

7. A compound of claim 1, wherein

R³ stands for pyridyl, or 1,2,3,4-tetrahydronaphthyl that is substituted by hydroxy, halogen, methyl or methoxy, or for the group

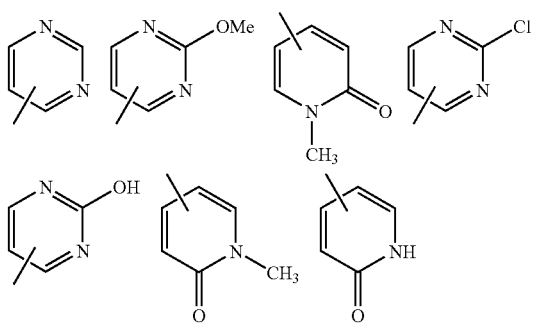

8. A compound of formula I

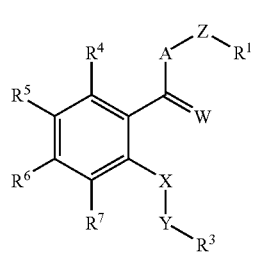

I wherein
A stands for the group =NR²,
W stands for oxygen,
Z stands for the group

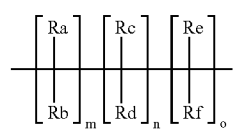

m, n and o stand for 0–3,
q stands for 1–6,
$R_a, R_b, R_c, R_d, R_e, R_f$, independently of one another, stand for hydrogen, methyl, or the group =NR¹⁰,
X stands for the group =NR⁹,
Y stands for the group —(CH₂)$_p$,
p stands for 1–4,
R¹ stands for naphthyl, biphenyl, phenyl, thiophenyl, furanyl, oxazolyl, thiazolyl, imidazolyl, pyrazolyl, pyridyl, pyrimidinyl, triazinyl, quinolinyl or isoquinolinyl that is unsubstituted or substituted in one or more places with halogen, $C_{1-6}$ alkyl or $C_{1-4}$-alkoxy, hydroxy, nitro, cyano or $C_{1-6}$-alkyl or $C_{1-6}$-alkoxy that is substituted in one or more places with halogen; or 5-chloro-2,3-dihydroindenyl, 2,3-dihydroindenyl, thienyl, 6-fluoro-1H-indol-3-yl, 1,2,3,4-tetrahydronaphthyl, benzo-1,2,5-oxadiazole, 6,7-dimethoxy-1,2,3,4-tetrahydro-2-naphthyl or for one of the groups

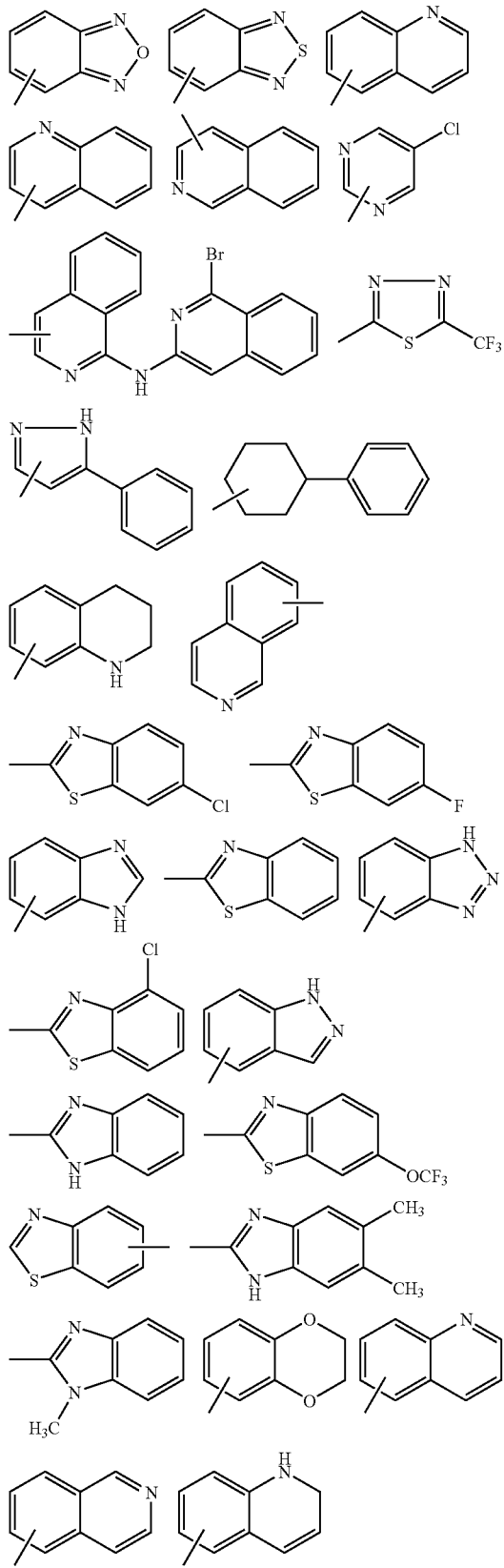

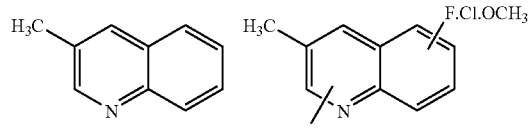

wherein an aryl group is not directly bonded to =NR² in the meaning of A,

R² stands for hydrogen or methyl,

R³ stands for naphthyl, biphenyl, thiophenyl, furanyl, oxazolyl, thiazolyl, imidazolyl, pyrazolyl, pyridyl, pyrimidinyl, triazinyl, quinolinyl or isoquinolinyl that is unsubstituted or substituted in one or more places with halogen, $C_{1-6}$ alkyl or $C_{1-6}$alkoxy or hydroxy, or for one of the groups

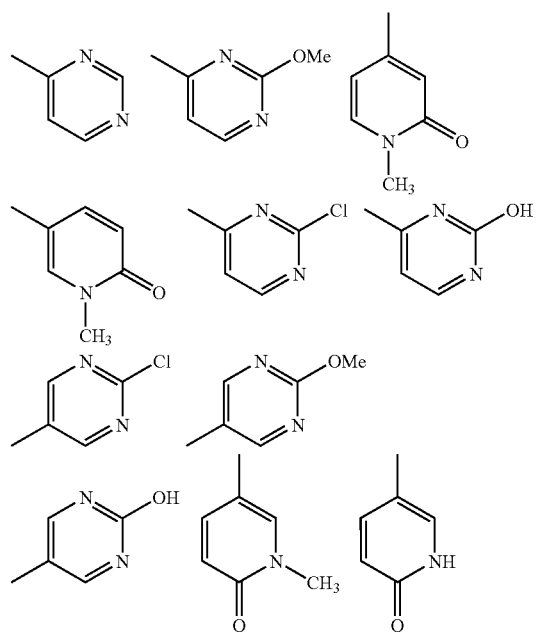

R⁴, R⁵, R⁶, and R⁷, independently of one another, stand for hydrogen, halogen, or $C_{1-6}$ alkoxy, $C_{1-6}$ alkyl or $C_{1-6}$ carboxylalkyl that is unsubstituted or substituted in one or more places with halogen, or R⁵ and R⁶ together form the group

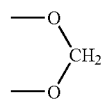

R⁸, R⁹, and R¹⁰, independently of one another, stand for hydrogen, halogen, or $C_{1-6}$ or an isomer or, pharmaceutically acceptable salt thereof.

9. A composition according to claim 1, wherein R³ is pyridyl or substituted pyridyl.

10. A composition according to claim 1, wherein R³ is a heteroaryl.

11. A pharmaceutical composition comprising a therapeutical effective amount of at least one compound according to claim 1 and a pharmaceutical acceptable carrier.

12. A method of producing a pharmaceutical preparation for enteral, parenteral and oral administration comprising mixing a compound of claim 1 with a suitable pharmaceutical carrier.

13. A method of inhibiting the tyrosine kinase KDR and/or FLT, comprising administering to a patient in need thereof a therapeutically effective amount of a compound according to claim 1.

14. A method of claim 13 wherein said patient is suffering from a disease or condition mediated by VEGF which is a tumor, psoriasis, arthritis, hemangioma, angiofibroma, an eye disease, neovascular glaucoma, a renal disease, a fibrotic disease, a mesangial-cell-proliferative disease, arteriosclerosis, an injury to the nerve tissue, and for inhibiting the reocclusion of a vessel after balloon catheter treatment, a vascular prosthetic or a mechanical device is used to keep a vessel open.

* * * * *

UNITED STATES PATENT AND TRADEMARK OFFICE
CERTIFICATE OF CORRECTION

PATENT NO. : 7,122,547 B1
APPLICATION NO. : 09/831506
DATED : October 17, 2006
INVENTOR(S) : Adreas Huth Page 1 of 1

It is certified that error appears in the above-identified patent and that said Letters Patent is hereby corrected as shown below:

Column 66, line 42 reads "$R_e$" should read --$R_c$--

Column 69, lines 65-67 reads "$R^3$ stands for monocyclic of bicyclic heteroaryl that is one of more places with halogen, $C_{1-6}$ alkyl, $C_{1-6}$ alkoxy or hydroxy," should read -- $R^3$ stands for monocyclic or bicyclic aryl or monocyclic or bicyclic heteroaryl that is unsubstituted or optionally substituted in one or more places with halogen, $C_{1-6}$ alkyl, $C_{1-6}$ alkoxy or hydroxy, --

Column 75, lines 20 reads "for hydrogen or methyl or" should read -- for hydrogen or methyl or the group $^=NR^{10}$, --

Column 82, lines 59-60 reads "hydrogen, halogen, or $C_{1-6}$ alkyl, or an isomer or, pharmaceutically acceptable salt thereof." should read -- hydrogen or $C_{1-6}$ alkyl, or an isomer or, pharmaceutically acceptable salt thereof. --

Signed and Sealed this

Seventeenth Day of April, 2007

JON W. DUDAS
*Director of the United States Patent and Trademark Office*